(12) United States Patent
Willson et al.

(10) Patent No.: US 7,078,174 B1
(45) Date of Patent: Jul. 18, 2006

(54) SCREENING METHODS USING SOCS BOX-CONTAINING PEPTIDES

(75) Inventors: Tracy Ann Willson, North Balwyn (AU); Richard John Simpson, Richmond (AU); Alison Mary Farley, Port Fairy (AU); Sandra Elaine Nicholson, Newport (AU); Jian-Guo Zhang, North Melbourne (AU); Manuel Baca, Ivanhoe (AU); Nicos A. Nicola, Mont Albert (AU); Douglas J. Hilton, Warrandyte (AU); Warren Scott Alexander, Moonee Ponds (AU); Donald Metcalf, Balwyn (AU)

(73) Assignee: The Walter & Eliza Hall Institute of Medical Research, Victoria (AU)

( * ) Notice: Subject to any disclaimer, the term of this patent is extended or adjusted under 35 U.S.C. 154(b) by 0 days.

(21) Appl. No.: 09/868,813

(22) PCT Filed: Dec. 21, 1999

(86) PCT No.: PCT/AU99/01134

§ 371 (c)(1),
(2), (4) Date: Feb. 26, 2002

(87) PCT Pub. No.: WO00/37636

PCT Pub. Date: Jun. 29, 2000

(30) Foreign Application Priority Data

Dec. 21, 1998 (AU) .................................. PP7841
Dec. 24, 1998 (AU) .................................. PP7950

(51) Int. Cl.
*G01N 33/53* (2006.01)
*G01N 33/567* (2006.01)

(52) U.S. Cl. ........................................ 435/7.1; 435/7.2
(58) Field of Classification Search ................. 435/7.1, 435/7.2
See application file for complete search history.

(56) References Cited

FOREIGN PATENT DOCUMENTS

| WO | WO 97/35978 | 10/1997 |
| WO | WO 98/14574 | 4/1998 |
| WO | WO 98/20023 | 5/1998 |
| WO | WO 99/03993 | 1/1999 |
| WO | WO 99/03994 | 1/1999 |
| WO | WO 99/40946 | 8/1999 |

OTHER PUBLICATIONS

Kamura T, et al. Genes & Development. 12:3872-3881, 1998.*
Robyn Star, et al. (1997) "A Family of Cytokine-inducible Inhibitors of Signalling", NATURE, vol. 387: 917-921.
Douglas J. Hilton, et al. (1998) "Twenty Proteins Containing a C-terminal SOCS Box Form Five Structural Classes", Proc. Natl. Acad. Sci., USA, vol. 95: 114-119.
Akihiko Yoshimura, et al. (1995) "A Novel Cytokine-inducible Gene CIS encodes an SH2-Containing Protein that Binds to Tyrosine-phosphorylated Interleukin 3 and Erythropoietin Receptors", The EMBO Journal, vol. 14, No. 12: 2816-2826.
Takaho A. Endo, et al. (1997) "A New Protein Containing an SH2 Domain that Inhibits JAK Kinases", NATURE, vol. 387, No. 26: 921-924.
Tetsuji Naka, et al. (1997) "Structure and Function of a New STAT-induced STAT Inhibitor", NATURE, vol. 387, No. 26: 924-929.
Masaaki Masuhara, et al. (1997) "Cloning and Characterization of Novel CIS Family Genes", Biochemical and Biophysical Research Communications, vol. 239: 439-446.
Seijiro Minamoto, et al. (1997) "Cloning and Functional Analysis of New Members of STAT Induced STAT Inhibitor (SSI) Family: SSI-2 and SSI-3", Biochemical and Biophysical Research Communications, vol. 237: 79-83.
Masashi Narazaki, et al. (1998) "Three Distinct Domains of SSI-1/SOCS-1/JAB Protein are Required for its Suppression of Interleukin 6 Signaling", Proc. Natl. Acad. Sci USA, vol. 95: 13130-13134.
Donald B. Smith, et al. (1988) "Single-Step Purification of Polypeptides Expressed in *Escherichia coli* as Fusions with Glutathione S-Transferase" Elsevier Science Publishers B.V. (Biochemical Division), vol. 67: 31-40.
Robert L. Moritz, et al. (1996) "S-Pyridylethylation of Intact Polyacrylamide Gels and in situ Digestion of Electrophoretically Separated Proteins: A Rapid Mass Spectrometric Method of Identifying Cysteine-Containing Peptides", Electrophuresis, vol. 17: 907-917.
Robert L. Moritz, et al. (1994) "Capillary HPLC: A Method for Protein Isolation and Peptide Mapping", METHODS: A Companion to Methods in Enzymology, vol. 6: 213-226.
Lisa M. Zugaro, et al., (1998) "Characterization of Rat Brain Stathmin Isoforms by Two-Dimensional Gel Electrophoresis-matrix Assisted Laser Desorption/Ionization and Electrospray Ionization-ion Trap Mass Spectrometry", Electrophoresis, vol. 19: 867-876.

(Continued)

*Primary Examiner*—Robert S. Landsman
(74) *Attorney, Agent, or Firm*—Scully, Scott, Murphy & Presser, P.C.

(57) ABSTRACT

The present invention relates generally to amino acid sequences obtainable from SOCS proteins and which are capable of interacting with intracellular molecules. The present invention further relates to nucleic acid molecules encoding said amino acid sequences. The amino acid sequences and the nucleic acid molecules encoding same of the present invention are useful in modulating degradation of proteinaceous molecules such as but not limited to SOCS proteins and proteinaceous molecules associated therewith. The present invention provides a mechanism for modulating cytokine or cytokine-like molecule signalling by modulating the degradation of activated signal transduction molecules or their negative regulators, i.e. the SOCS proteins.

2 Claims, 8 Drawing Sheets

OTHER PUBLICATIONS

Figure 1:
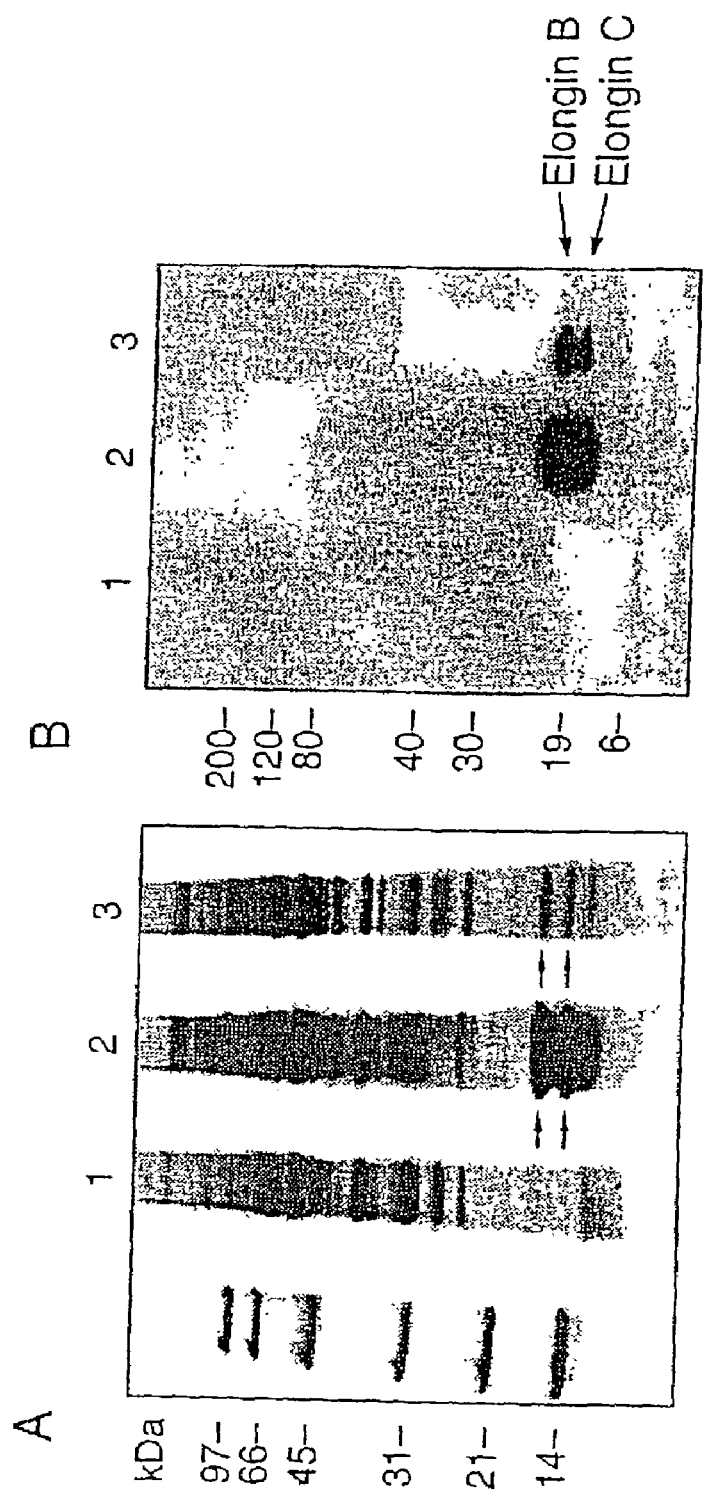

Jimmy K. Eng, et al., (1994) "An Approach to Correlate Tandem Mass Spectral Data of Peptides with Amino Acid Sequences in a Protein Database", J Am. Soc. Mass Spectrum, vol. 5: 976-989.

Martina Schnolzer, et al. (1992) "In situ Neutralization in Boc-Chemistry Solid Phase Peptide Synthesis", Int. J. Peptide Protein Res., vol. 0: 1-15.

William G. Kaelin, Jr. (1998) "The VHL Tumour-Suppressor Gene Paradigm", TIG, vol. 14, No. 10: 423-426.

Joan W. Conaway, et al. (1998) "The Elongin BC Complex and the Von Hippel-Lindau Tumor Suppressor Protein", Biochimica et Biophysica Acta 1377:M49-M54.

Karla P. Garrett, et al. (1995) "Positive Regulation of General Transcuiption Factor SIII by a Tailed Ubiquitin Homolog", Proc. Natl. Acad. Sci. USA, vol. 92: 7172-7176.

Kim M. Lonergan, et al. (1998) "Regulation of Hypoxia-Inducible mRNAs by the von Hippel-Lindau Tumor Suppressor Protein Requires Binding to Complexes Containing Elongins B/C and Cul2", Molecular and Cellular Biology, p. 732-741.

Cherylene Schauber, et al. (1998) "Rad23 Links DNA Repair to the Ubiquitin/Proteasome Pathway", Nature, vol. 391: 715-718.

D. Roxanne Duan, et al. (1995) "Inhibition of Transcription Elongation by the VHL Tumor Suppressor Protein", Science, vol. 269: 1402-1406.

Adam Kibel, et al. (1995) "Binding of the von Hippel-Landau Tumor Suppressor Protein to Elongin B and C", Science, vol. 269: 1444-1446.

Arnim Pause, et al. (1997) "The von Hippel-Landau Tumor-Suppressor Gene Product Forms a Stable Complex with Human CUL-2, a Member of the Cdc53 Family of Proteins", Proc. Natl. Acad. Sci., USA, vol. 94: 2156-2161.

Takeshi Kishida, et al. (1995) "Cellular Proteins that Bind the von Hippel-Lindau Disease Gene Product: Maping of Binding Domains and the Effect of Missense Mutations", Cancer Research, vol. 55: 4544-4548.

Avram Hershko, et al. (1998) "The Ubiquitin System", Annu. Rev. Biochem., vol. 67: 425-479.

Frederique Verdier, et al. (1998) "Proteasomes Regulate Erythropoietin Receptor and Signal Transducer and Activators of Transcription 5 (STAT5) Activation", The Journal of Biological Chemistry, vol. 273, No. 43: 28185-28190.

Chao-Lan Yu, et al. (1997) "Involvement of Proteasomes in Regulating Jak-STAT Pathways Upon Interleukin-2 Stimulation", The Journal of Biological Chemistry, vol. 272, No. 22: 14017-14020.

Jennifer Terrell, et al. (1998) "A Function for Monoubiquitination in the Internalization of a G Protein-Coupled Receptor", Molecular Cell, vol. 1: 193-202.

Kamura, T., et al. (1998) "The Elongin BC complex interacts with the conserved SOCS-box motif present in members of the SOCS, ras, WD-40 Repeat, and ankyrin repeat families", *Gene Dev 12*(24): 3872-3881.

Zhang, J. G., et al. (1999) "The conserved SOCS box motif in suppressors of cytokine signaling binds to elongins B and C and may couple bound proteins to proteasomal degradation", *Proc Natl Acad Sci USA* 96(5):2071-2076.

Alexander, W.S., et al. (1999) "Suppressors of cytokine signaling (Socs) : negative regulators of signal transduction", *J. Leukoc Biol 66*(4): 588-592.

Alexander, W.S., et al. (1999) "SOCS 1 Is a Critical Inhibitor of Interferon γ Signaling and Prevents the Potentially Fatal Neonatal Actions of this Cytokine" *Cell 98*(5): 597-608.

Bousquet, C., et al. (1999) "Inhibitory roles for SHP-1 and SOCS-3 following pituitary proopiomelanocortin induction by leukemia inhibitory factor" *J. Clin Invest 104*(9): 1277-1285.

* cited by examiner

SEQUENCE LISTING

```
<160> NUMBER OF SEQ ID NOS: 6

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: FLAG
      epitope tag

<400> SEQUENCE: 1

Asp Tyr Lys Asp Asp Asp Lys
 1               5

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: myc
      epitope tag

<400> SEQUENCE: 2
```

-continued

Asp Gln Lys Leu Ile Ser Glu Glu Asp Leu
 1               5                  10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: linker
      sequence

<400> SEQUENCE: 3

Glu Gly Lys Ser Ser Gly Ser Gly Ser Glu Ser Lys Val Asp
 1               5                  10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: consensus
      sequence in the N-terminus of SOCS boxes
<220> FEATURE:
<221> NAME/KEY: misc_feature
<222> LOCATION: (1)
<223> OTHER INFORMATION: Xaa is Thr, Ser or Pro
<220> FEATURE:
<221> NAME/KEY: misc_feature
<222> LOCATION: (3)..(5)
<223> OTHER INFORMATION: Xaa is any amino acid
<220> FEATURE:
<221> NAME/KEY: misc_feature
<222> LOCATION: (6)
<223> OTHER INFORMATION: Xaa is Cys or Ser
<220> FEATURE:
<221> NAME/KEY: misc_feature
<222> LOCATION: (7)..(9)
<223> OTHER INFORMATION: Xaa is any amino acid
<220> FEATURE:
<221> NAME/KEY: misc_feature
<222> LOCATION: (10)
<223> OTHER INFORMATION: Xaa is Leu, Ile or Val

<400> SEQUENCE: 4

Xaa Leu Xaa Xaa Xaa Xaa Xaa Xaa Xaa Xaa
             5                  10

<210> SEQ ID NO 5
<211> LENGTH: 128
<212> TYPE: PRT
<213> ORGANISM: Mus musculus
<220> FEATURE:
<221> NAME/KEY: UNSURE
<222> LOCATION: (1)
<223> OTHER INFORMATION: Xaa is Leu, Ile, Val, Met, Ala or Pro
<220> FEATURE:
<221> NAME/KEY: UNSURE
<222> LOCATION: (2)
<223> OTHER INFORMATION: Xaa is any amino acid residue
<220> FEATURE:
<221> NAME/KEY: UNSURE
<222> LOCATION: (3)
<223> OTHER INFORMATION: Xaa is Pro, Thr or Ser
<220> FEATURE:
<221> NAME/KEY: UNSURE
<222> LOCATION: (4)
<223> OTHER INFORMATION: Xaa is Leu, Ile, Val, Met, Ala or Pro
<220> FEATURE:
<221> NAME/KEY: UNSURE
<222> LOCATION: (5)
<223> OTHER INFORMATION: Xaa is any amino acid
<220> FEATURE:
<221> NAME/KEY: UNSURE
<222> LOCATION: (6)

```
-continued

<223> OTHER INFORMATION: Xaa is any amino acid
<220> FEATURE:
<221> NAME/KEY: UNSURE
<222> LOCATION: (7)
<223> OTHER INFORMATION: Xaa is Leu, Ile, Val, Met, Ala, Phe, Tyr or Trp
<220> FEATURE:
<221> NAME/KEY: UNSURE
<222> LOCATION: (8)
<223> OTHER INFORMATION: Xaa is Cys, Thr or Ser
<220> FEATURE:
<221> NAME/KEY: UNSURE
<222> LOCATION: (9)
<223> OTHER INFORMATION: Xaa is Arg, Lys or His
<220> FEATURE:
<221> NAME/KEY: UNSURE
<222> LOCATION: (10)
<223> OTHER INFORMATION: Xaa is any amino acid
<220> FEATURE:
<221> NAME/KEY: UNSURE
<222> LOCATION: (11)
<223> OTHER INFORMATION: Xaa is any amino acid
<220> FEATURE:
<221> NAME/KEY: UNSURE
<222> LOCATION: (12)
<223> OTHER INFORMATION: Xaa is Leu, Ile, Val, Met, Ala or Pro
<220> FEATURE:
<221> NAME/KEY: UNSURE
<222> LOCATION: (13)
<223> OTHER INFORMATION: Xaa is any amino acid
<220> FEATURE:
<221> NAME/KEY: UNSURE
<222> LOCATION: (14)
<223> OTHER INFORMATION: Xaa is any amino acid
<220> FEATURE:
<221> NAME/KEY: UNSURE
<222> LOCATION: (15)
<223> OTHER INFORMATION: Xaa is any amino acid
<220> FEATURE:
<221> NAME/KEY: UNSURE
<222> LOCATION: (16)
<223> OTHER INFORMATION: Xaa is Leu, Ile, Val, Met, Ala, Pro, Gly, Cys,
      Thr or Ser
<220> FEATURE:
<221> NAME/KEY: UNSURE
<222> LOCATION: (17)..(66)
<223> OTHER INFORMATION: Xaa can be any amino acid. Position 17-66
      can be 1-50 amino acids.
<220> FEATURE:
<221> NAME/KEY: UNSURE
<222> LOCATION: (67)
<223> OTHER INFORMATION: Xaa is Leu, Ile, Val, Met, Ala or Pro
<220> FEATURE:
<221> NAME/KEY: UNSURE
<222> LOCATION: (68)
<223> OTHER INFORMATION: Xaa is any amino acid
<220> FEATURE:
<221> NAME/KEY: UNSURE
<222> LOCATION: (69)
<223> OTHER INFORMATION: Xaa is any amino acid
<220> FEATURE:
<221> NAME/KEY: UNSURE
<222> LOCATION: (70)
<223> OTHER INFORMATION: Xaa is Leu, Ile, Val, Met, Ala or Pro
<220> FEATURE:
<221> NAME/KEY: UNSURE
<222> LOCATION: (72)
<223> OTHER INFORMATION: Xaa is Leu, Ile, Val, Met, Ala, Pro or Gly
<220> FEATURE:
<221> NAME/KEY: UNSURE
<222> LOCATION: (73)
<223> OTHER INFORMATION: Xaa is Pro or Asn
<220> FEATURE:
<221> NAME/KEY: UNSURE
<222> LOCATION: (74)..(123)
<223> OTHER INFORMATION: Xaa can be any amino acid. Position 74-123
      can be 1-50 amino acids.
<220> FEATURE:
<221> NAME/KEY: UNSURE
<222> LOCATION: (124)
```

```
<223> OTHER INFORMATION: Xaa is Leu, Ile, Val, Met, Ala or Pro
<220> FEATURE:
<221> NAME/KEY: UNSURE
<222> LOCATION: (125)..(126)
<223> OTHER INFORMATION: Xaa is any amino acid
<220> FEATURE:
<221> NAME/KEY: UNSURE
<222> LOCATION: (127)
<223> OTHER INFORMATION: Xaa is Tyr or Phe
<220> FEATURE:
<221> NAME/KEY: UNSURE
<222> LOCATION: (128)
<223> OTHER INFORMATION: Xaa is Leu, Ile, Val, Met, Ala or Pro

<400> SEQUENCE: 5

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
       50                  55                  60

Xaa Xaa Xaa Xaa Xaa Xaa Pro Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
           100                 105                 110

Xaa Xaa Xaa Xaa Xaa Xaa Xaa Xaa Xaa Xaa Xaa Xaa Xaa Xaa Xaa Xaa
       115                 120                 125

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: a
      protein-protein interaction domain in SOCS proteins

<400> SEQUENCE: 6

Ser Pro Arg Tyr
```

SCREENING METHODS USING SOCS BOX-CONTAINING PEPTIDES

The present invention relates generally to amino acid sequences obtainable from SOCS proteins and which are capable of interacting with intracellular molecules. The present invention further relates to nucleic acid molecules encoding said amino acid sequences. The amino acid sequences and the nucleic acid molecules encoding same of the present invention are useful in modulating degradation of proteinaceous molecules such as but not limited to SOCS proteins and proteinaceous molecules associated therewith. The present invention provides a mechanism for modulating cytokine or cytokine-like molecule signalling by modulating the degradation of activated signal transduction molecules or their negative regulators, i.e. the SOCS proteins.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Bibliographic details of the publications numerically referred to in this specification are collected at the end of the description.

Cells continually monitor their environment in order to modulate physiological and biochemcial processes which in turn affects future behaviour. Frequently, a cell's initial interaction with its surroundings occurs via receptors expressed on the plasma membrane. Activiation of these receptors, whether through binding endogenous ligands (such as cytokines) or exogenous ligands (such as antigens), triggers a biochemical cascade from the membrane through the cytoplasm to the nucleus.

Of the endogenous ligands, cytokines represent an important and versatile group. However, of particular importance are molecules which regulate cytokine function. An example of this class of molecules are members of the family of suppressors of cytokine signalling (SOCS).

SOCS proteins contain a central SH2 domain and a C-terminal homology domain we have termed the SOCS box (1). The first family was called CIS (cytokine-inducible SH2-containing protein) (2) and was shown to inhibit erythropoietin and interleukin-3 receptor signalling. The inventors cloned SOCS-1 from a retroviral expression library as a cDNA whose constitutive expression inhibited interleukin-6-induced differentiation of MI cells and it was simultaneously cloned as a protein that interacted with activated JAK kinases (JAK-binding protein, JAB) (3) and as a protein with antigenic similarity to STATs (STAT-inducible STAT inhibitor, SSI) (4). The sequence similarity of SOCS-1 and CIS led to the identification of six additional members of this family (SOCS-2–7) each with an SH2 domain and a C-terminal SOCS box (1,5,6). An additional twelve proteins have been described that contain a C-terminal SOCS box but instead of an SH2 domain they contain different protein—protein interaction domains including WD40, ankyrin repeats, SPRY (SEQ ID NO: 6) or small GTPase domains (1).

Following binding to their receptors, many cytokines activate receptor-associated cytoplasmic kinases called JAKs which in turn phosphorylate the receptor cytoplasmic domain and associated signal transducers and activators of transcription (STATs). Phosphorylated STAT dimers translocate to the nucleus and activate transcription of specific genes including those of CIS and some of the SOCS. SOCS proteins then recognize activated signalling molecules (including JAKs and cytokine receptors) through their SH2 and N-terminal domains and inhibit their activity (7,8). Exactly how SOCS proteins inhibit JAK kinase activity and the role of the conserved SOCS box are currently unknown.

The present invention is predicated in part on the demonstration that the SOCS box in proteins facilitates the presentation of proteins bound to the SOCS box to the ubiquitination and/or proteasomal compartments. Generally, the presentation of proteins to these compartments requires elongin B and/or elongin C. Accordingly, the present invention proposes that SOCS-box-containing proteins form a family of adapter proteins which terminate cell signalling by targeting critical molecules for intracellular degradation.

The elucidation of the mechanism of action of the SOCS box permits the development of a range of molecules which are capable of modulating SOCS proteins and of molecules associated herewith. In addition, the SOCS box itself provides a means of inducing protein degradation when introduced into a target peptide, polypeptide or protein.

Accordingly, one aspect of the present invention contemplates a method for facilitating the termination of cell signalling by a cytokine or cytokine-like molecule, said method comprising promoting interaction between said cytokine or cytokine-like molecule, a SOCS-box-containing peptide, polypeptide or protein or a chemical analogue thereof and one or more other molecules wherein the resulting complex is subjected to degradation via the ubiquitination or proteasomal compartments.

In a related embodiment, the present invention provides for the use of a SOCS-box-containing peptide, polypeptide or protein or a chemical analogue thereof together with one or more other molecules to couple said SOCS-box-containing peptide, polypeptide or protein and/or one or more other molecules to the ubiquitination or proteasomal compartments thereby terminating or substantially reducing cytokine- or cytokine-like molecule-mediated cell signalling.

Preferably, the at least one other molecule involved in the complex with a SOCS-box-containing peptide, polypeptide or protein is involved in cytokine or cytokine-like molecule signalling such as but not limited to elongin B and/or elongin C or functional equivalents or chemical analogues thereof or is a molecule capable of interacting with elongin B and/or elongin C such as but not limited to elongin A or its functional equivalent or chemical analogue. Alternatively, the complex comprising elongin B, C and/or A may also bind or otherwise interact with von Hippel Lindau (VHL) tumor suppressor protein (15,16). It is proposed, in accordance with the present invention, that degradation of SOCS-box-containing molecules and/or other molecules terminates signalling by a cytokine or cytokine-like molecule.

According to a preferred embodiment, the present invention is directed to a method for facilitating the termination of cell signalling by a cytokine or cytokine-like molecule, said method comprising promoting interaction between a SOCS-box-containing peptide, polypeptide or protein or a functional equivalent or chemical analogue thereof and at least two of the following groups of molecules:—

(i) elongin B or a functional equivalent or chemical analogue thereof;
(ii) elongin C or a functional equivalent or chemical analogue thereof;
(iii) elongin A or a functional equivalent or chemical analogue thereof;
(iv) VHL or a functional equivalent or chemical analogue thereof;
(v) elongins B and C or their functional equivalents or chemical analogues;

(vi) elongins B, C and A or their functional equivalents or chemical analogues;
(vii) elongins B and C and VHL or their functional equivalents or chemical analogues; and/or
(viii) elongins B, C and A and VHL or their functional equivalents or chemical analogues;

wherein the resulting complex is subjected to degradation via ubiquitination or proteasomal compartments.

In a particularly preferred embodiment, the interaction is between at least three of the above groups of molecules.

Another aspect of the present invention contemplates a nucleic acid molecule encoding or complementary to a sequence encoding an amino acid sequence which is capable of interacting with elongin B and/or elongin C.

More particularly, the present invention provides a nucleic acid molecule encoding or complementary to a sequence encoding an amino acid sequence which is capable of interacting with elongin B and/or elongin C or their homologues to form a complex wherein said complex facilitates degradation of said amino acid sequence and any other proteinaceous molecule associated with said amino acid sequence.

In a particularly preferred embodiment, the present invention provides a nucleic acid molecule encoding the amino acid sequence:

$X_1 X_2 X_3 X_4 X_5 X_6 X_7 X_8 X_9 X_{10} X_{11} X_{12} X_{13} X_{14} X_{15} X_{16}$ $[Xi]_n X_{17} X_{18} X_{19} X_{20} X_{21} X_{22} X_{23} [Xj]_n X_{24} X_{25} X_{26} X_{27} X_{28}$ (SEQ ID NO:5)

wherein:
$X_1$ is L, I, V, M, A or P;
$X_2$ is any amino acid residue;
$X_3$ is P, T or S;
$X_4$ is L, I, V, M, A or P;
$X_5$ is any amino acid;
$X_6$ is any amino acid;
$X_7$ is L, I, V, M, A, F, Y or W;
$X_8$ is C, T or S;
$X_9$ is R, K or H;
$X_{10}$ is any amino acid;
$X_{11}$ is any amino acid;
$X_{12}$ is L, I, V, M, A or P;
$X_{13}$ is any amino acid;
$X_{14}$ is any amino acid;
$X_{15}$ is any amino acid;
$X_{16}$ is L, I, V, M, A, P, G, C, T or S;
$[Xi]_n$ is a sequence of n amino acids wherein n is from 1 to 50 amino acids and wherein the sequence Xi may comprise the same or different amino acids selected from any amino acid residue;
$X_{17}$ is L, I, V, M, A or P;
$X_{18}$ is any amino acid;
$X_{19}$ is any amino acid;
$X_{20}$ L, I, V, M, A or P;
$X_{21}$ is P;
$X_{22}$ is L, I, V, M, A, P or G;
$X_{23}$ is P or N;
$[Xj]_n$ is a sequence of n amino acids wherein n is from 1 to 50 amino acids and wherein the sequence Xj may comprise the same or different amino acids selected from any amino acid residue;
$X_{24}$ is L, I, V, M, A or P;
$X_{25}$ is any amino acid;
$X_{26}$ is any amino acid;
$X_{27}$ is Y or F;
$X_{28}$ is L, I, V, M, A or P.

wherein said amino acid sequence is capable of interacting with elongin B and/or elongin C or their homologues to form a complex wherein said complex facilitates degradation of said amino acid sequence and any other proteinaceous molecule associated with said amino acid sequence.

The terms "SOCS" and "SOCS protein" are used in their broadest context. SOCS proteins are defined in International Patent Application No. PCT/AU97/00729 filed 31 Oct. 1997 and published 14 May, 1998 under serial number WO98/20023. This International application is incorporated herein by reference.

The amino acid sequence capable of interacting with elongins B and C is a referred to herein as the SOCS box. Reference herein for a "SOCS box" includes reference to mutants, derivatives, homologues, analogues and functional equivalents thereof. The nucleic acid molecule of the present invention may encode a SOCS protein comprising the elongins B and C-interacting region (i.e. SOCS box) or may encode a peptide, polypeptide or protein which is heterologous to this region. The nucleic acid molecule may also encode a peptide comprising solely the elongins B and C-interacting region.

The present invention further contemplates a peptide, polypeptide or protein comprising a sequence of amino acids which is capable of interacting with elongin B and elongin C.

More particularly, the present invention is directed to a peptide, polypeptide or protein comprising a sequence of amino acids capable of interacting with elongin B and elongin C or their homologues to form a complex wherein said complex facilitates degradation of said amino acid sequence and any other proteinaceous molecule associated with said peptide, polypeptide or protein.

Still more particularly, the present invention provides a peptide, polypeptide or protein comprising the amino acid sequence:

$X_1 X_2 X_3 X_4 X_5 X_6 X_7 X_8 X_9 X_{10} X_{11} X_{12} X_{13} X_{14} X_{15} X_{16}$ $[Xi]_n X_{17} X_{18} X_{19} X_{20} X_{21} X_{22} X_{23} [Xj]_n X_{24} X_{25} X_{26} X_{27} X_{28}$ (SEQ ID NO: 5)

wherein:
$X_1$ is L, I, V, M, A or P;
$X_2$ is any amino acid residue;
$X_3$ is P, T or S;
$X_4$ is L, I, V, M, A or P;
$X_5$ is any amino acid;
$X_6$ is any amino acid;
$X_7$ is L, I, V, M, A, F, Y or W;
$X_8$ is C, T or S;
$X_9$ is R, K or H;
$X_{10}$ is any amino acid;
$X_{11}$ is any amino acid;
$X_{12}$ is L, I, V, M, A or P;
$X_{13}$ is any amino acid;
$X_{14}$ is any amino acid;
$X_{15}$ is any amino acid;
$X_{16}$ is L, I, V, M, A, P, G, C, T or S;
$[Xi]_n$ is a sequence of n amino acids wherein n is from 1 to 50 amino acids and wherein the sequence Xi may comprise the same or different amino acids selected from any amino acid residue;
$X_{17}$ is L, I, V, M, A or P;
$X_{18}$ is any amino acid;
$X_{19}$ is any amino acid;
$X_{20}$ L, I, V, M, A or P;
$X_{21}$ is P;
$X_{22}$ is L, I, V, M, A, P or G;
$X_{23}$ is P or N;

[Xj]$_n$ is a sequence of n amino acids wherein n is from 1 to 50 amino acids and wherein the sequence Xj may comprise the same or different amino acids selected from any amino acid residue;

$X_{24}$ is L, I, V, M, A or P;

$X_{25}$ is any amino acid;

$X_{26}$ is any amino acid;

$X_{27}$ is Y or F;

$X_{28}$ is L, I, V, M, A or P.

wherein said amino acid sequence is capable of interacting with elongin B and/or elongin C or their homologues to form a complex wherein said complex facilitates degradation of said amino acid sequence and any other proteinaceous molecule associated with said peptide, polypeptide or protein.

The nucleic acid molecule and peptides, polypeptides and proteins of the present invention are preferably in isolated or purified form. The terms "isolated" and "purified" mean that the molecule has undergone at least one purification step away from other material. With respect to nucleic acid molecules, these are generally in the form of DNA such as cDNA or genomic DNA. The DNA may encode the same amino acid sequence as the naturally occurring elongins B and C-interacting region or a region containing one or more amino acid substitutions, deletions and/or additions. The nucleotide sequence may correspond to the genomic coding sequence (including exons and introns) or to the nucleotide sequence in cDNA form or it may carry one or more nucleotide substitutions, deletions and/or additions thereto.

Although not intending to limit the present invention to any one theory or mode of action, it is proposed that the elongins B and C interacting region corresponds to all or part of the SOCS box of SOCS proteins.

One aspect of the present invention is now described by way of a specific example. The following description is not intended to limit the instant invention to this specific embodiment although the subject description does represent one preferred embodiment.

The present inventors have shown that a common role of SOCS boxes from several different classes of proteins is to bind to elongins B and C. The elongin B and C complex has previously been shown to bind to elongin A to from an active transcriptional elongation complex or to the von Hippel Lindau (VHL) tumor suppressor protein (15, 16). The sites on elongin A and VHL which interact with elongin C have been mapped and the consensus binding sequence (T,S,P) LXXX(C,S)XXZX(LIV) (SEQ ID NO:4) is also conserved in the N-terminal half of all SOCS boxes (16).

The elongin B/C complex appears to have two distinct roles. When bound to elongin A, it acts as a positive transcriptional regulator by increasing the activity of the RNA polymerase II elongation complex (II) but when bound to VHL, it acts to suppress the accumulation of hypoxia-inducible mRNAs (18). The VHL/elongin B/C complex contains a putative E3 ubiquitin ligase (Cullin-2) that targets VHL-binding proteins to destruction by the proteasome.

Cullin-2 appears to interact with elongin C (directly or indirectly) independently of subsequent association with VHL. Elongin B also contains a ubiquitin-like (UBL) sequence at its N-terminus (18) in common with several other proteins. One of these (RAD23) has recently been shown to interact directly with proteasomal subunit proteins (Cim3 and Cim5) through its UBL domain leading to an increase of protease activity associated with RAD23 (19). Analysis of the VHL gene in individuals with VHL disease has revealed that the interaction domain with elongin C is commonly mutated and that most affected individuals show a reduced ability of VHL to interact with elongins B and C (20–23). Similarly, mutation of the UBL domain in RAD23 in yeast leads to ultraviolet light sensitivity indicating that it plays an important regulatory role in nucleotide excision repair (19). These observations suggest that coupling of VHL or RAD23 proteins to the proteasome is essential for the correct functioning of these proteins.

Figure 6:
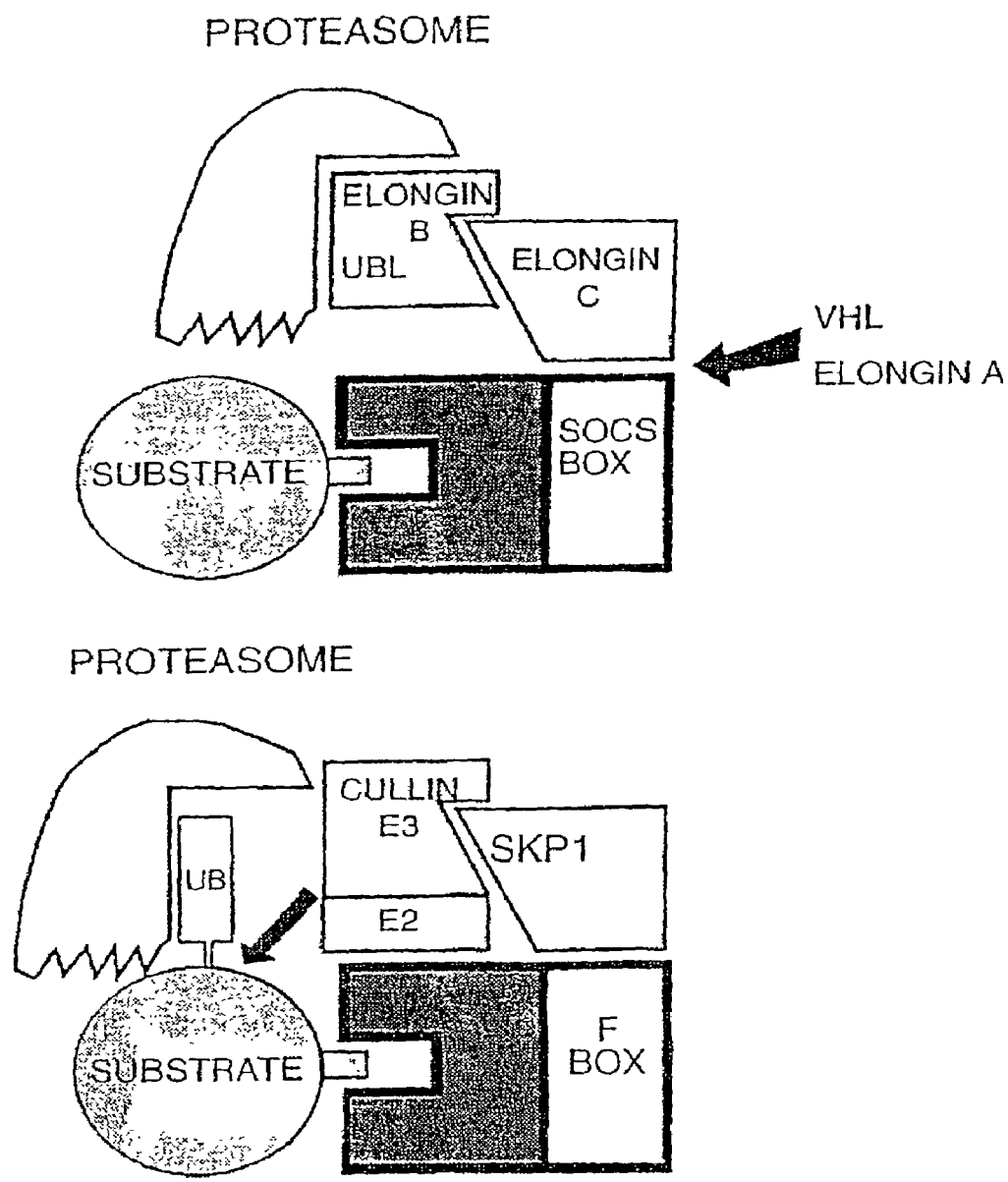

Put together with the inventors' data on the binding of elongin B/C to the SOCS box, these observations provide a model for the action of the SOCS proteins (FIG. 6). As previously shown (8), the N-terminal and SH2 domains of SOCS-1 and SOCS-3, at least, are required for recognition and binding to activated (tyrosine phosphorylated) signal transduction molecules (e.g. JAKs). The SOCS box brings into this complex elongins B and C and either through direct interactions of the elongin B UBL domain with the proteasome or through associated Cullin-2-induced ubiquitination of substrates and subsequent proteosomal association, the substrate and associated SOCS protein may be destroyed. In this scheme, both activated signal transduction molecules and their negative regulators (SOCS proteins) would be destroyed after a cytokine activation cycle and the cell would be ready to respond again if cytokine is still present.

In over-expression studies, the SOCS box was not required to inhibit cytokine signalling (7,8). This implies that SOCS interaction with its targets is sufficient to inhibit signalling and that the role of the SOCS box interaction with elongins B and C may be primarily to terminate the inhibitory signal by destroying the SOCS protein. The present data indicate that the SOCS box confers protein instability on SOCS-3 in a proteasome-dependent manner. In situations where SOCS proteins are expressed at physiological levels, the ability to degrade SOCS-associated signalling molecules may become important in order to achieve maximal inhibition of cytokine-generated signals.

It was also noted in the present study that intact SOCS proteins bound less well to elongins B and C than did isolated SOCS box peptides (at least for SOCS-1 and SOCS-3). This may suggest that SOCS box availability for interaction with elongins is dependent on conformational changes associated with SOCS protein binding to its activated targets (e.g. JAKs). Given the efficiency of the proteosomal protein degradation system, it may make some sense for SOCS proteins and signal transduction molecules to be destroyed only after they have interacted with their targets.

The model proposed herein for the function of the SOCS box has a parallel with components of the phosphoprotein-ubiquitin ligase complex (PULC) that is utilized to control various aspects of the cell cycle (24). In the yeast PULC system, serine phosphorylation of the cyclin-dependent kinase (cdk) inhibitor sicI or G1 cyclins Cln1 and Cln2 leads to their recognition by adaptor proteins such as Cdc4 or Grr1 which contain conserved N-terminal domains called F-Boxes. The F-Box mediates interaction with Skp1, an elongin C homologue, which in turn interacts with E2 and E3 (Cullin homologue) ubiquitin ligases. This results in ubiquitination of the phosphorylated substrates and targeting for proteasomal degradation so that the cell cycle can progress from G1 to S.

Recently, Verdier et al. (25) showed that CIS, a member of the SOCS family of proteins, is monoubiquinated and subjected to proteasomal degradation. Moreover, they also showed that inhibitors of the proteasome lead to sustained expression of activated forms of the erythropoietin receptor and STATS following erythropoietin stimulation of UT-7 cells. Similarly, Yu and Burakoff (26) showed that inhibition of the proteasome resulted in sustained activation of the JAK/STAT pathway following interleukin-w stimulation although neither appeared to be ubiquitinated. The present results provide a mechanism for targeting such proteins to proteasomal degradation via association of signalling molecules with the SOCS/CIS proteins followed by SOCS-box-mediated interaction with elongins B and C. This interaction results in ubiquitination of SOCS/CIS and associated molecules (mediated by cullins) or non-ubiquitinated proteins in the complex are delivered to the proteasome via the UBL sequence in elongin B. Another function of monoubiquitination of receptors is to target them to endocytosis and subsequent degradation by lysozymes rather than the proteasome (27). Consequently coupling of cell signalling molecules to the ubiquitination pathway can lead to termination of the signalling response in several different ways.

The present invention demonstrates, therefore, that the signal conserved domain in 20 structurally diverse proteins (the SOCS box) serves to couple bound proteins to the ubiquitination or proteasomal compartment through interaction with elongins B and C. The SOCS-box-containing proteins thus form a family of adapter proteins which terminate cell signalling by targeting critical molecules for intracellular degradation.

The present invention is particularly directed to facilitating the promotion of termination of cytokine- or cytokine-like molecule-mediated cell signalling. However, in various circumstances such as in the treatment of cancer or other disorders, it may be necessary to promote the continuation of signalling rather than terminating the signalling. Accordingly, the present invention provides agonists and antagonists of cytokine stimulation.

Another aspect of the present invention provides, therefore, an agonist or antagonist of cytokine- or cytokine-like molecule-mediated cell signalling, said agonist or antagonist facilitating or otherwise promoting or reducing or otherwise preventing complex formation between two or more of:—
(i) a SOCS-box-containing peptide, polypeptide or protein or functional equivalent thereof or chemical analogue thereof;
(ii) elongin B and/or C or functional equivalent thereof or chemical analogue thereof; and/or
(iii) elongin A and/or VHL or functional equivalent thereof or chemical analogue thereof.

The agonist or antagonist may be an isolated, purified naturally occurring molecule such as identified following natural product screening of, for example, aquatic or terrestrial plants, micro-organisms, coral, and/or sea or river beds. Alternatively, the agonist or antagonist may be identified following screening of chemical libraries. Yet in a further alternative, the agonist or antagonist may be a chemical analogue of a participant in the complex formation, for example, the agonist or antagonist may be a chemical analogue of one or more of elongin A, B or C, VHL, cytokine or a SOCS box.

In this context, a chemical analogue may also be a chemical derivative or may be a single or multiple amino acid substitution, addition and/or deletion to a member of the complex.

It is also proposed in accordance with the present invention to use the SOCS box to target peptides, polypeptide or proteins for degradation. This has utility in gene therapy in which a gene is engineered with SOCS box DNA at the 3'-end. The fusion protein then has a SOCS box at the C-terminus and targets the protein for degradation. If the N-terminal end of the fusion protein interacts with gene causing disease then this would also be targeted for degradation. Examples of this include oncogenes or viral proteins.

SOCS box peptides are also contemplated herein for use in blocking degradation of proteins. In accordance with that aspect of the present invention SOCS box peptides are delivered into the cytoplasm and these bind elongins and prevent other proteins from being degraded. This is advantageous to, for example, prolonging the half-life of endogenous SOCS proteins so that cytokine signalling is reduced, such as in inflammatory or autoimmune disease.

It is further contemplated by the present invention to use the SOCS box elongin C interaction as a molecular screen to isolate small molecule inhibitors of this interaction. Again, prolonging the half-life of SOCS proteins is one outcome. If, however, the small molecule recognized the site of elongin C, then protein turnover would be more generally inhibited, which is important in increasing the half life of proteins produced via gene therapy or in some cases preventing degradation of recombinant proteins produced in eukaryotic cells, where these proteins might be degraded by the proteasome pathway.

The present invention further contemplates other molecules associated with elongin B and elongin C interaction with the SOCS box and their use in modulating the function of the SOCS box, especially in mediating its own degradation following the formation of a complex with elongin B and C.

The nucleic acid molecule of the present invention may be isolated from any animal such as humans, primates, livestock animals (e.g. horses, cows, sheep, donkeys, pigs), laboratory test animals (e.g. mice, rats, rabbits, hamsters, guinea pigs), companion animals (e.g. dogs, cats) or captive wild animals (e.g. deer, foxes, kangaroos).

The terms "derivatives" or its singular form "derivative" whether in relation to a nucleic acid molecule or a protein includes parts, mutants, fragments and analogues as well as hybrid or fusion molecules and glycosylation variants. Particularly useful derivatives comprise single or multiple amino acid substitutions, deletions and/or additions to the SOCS box amino acid sequence.

Preferably, the derivatives have functional activity or alternatively act as antagonists or agonists. The present invention further extends to homologues of the SOCS box which include the functionally or structurally related molecules from different animal species. The present invention also encompasses analogues and mimetics. Mimetics include a class of molecule generally but not necessarily having a non-amino acid structure and which functionally are capable of acting in an analogous manner to the protein for which it is a mimic, in this case, a SOCS box. Mimetics may comprise a carbohydrate, aromatic ring, lipid or other complex chemical structure or may also be proteinaceous in composition. Mimetics as well as agonists and antagonists contemplated herein are conveniently located through systematic searching of environments, such as coral, marine and freshwater river beds, flora and microorganisms. This is sometimes referred to as natural product screening. Alternatively, libraries of synthetic chemical compounds may be screened for potentially useful molecules.

The present invention further extends to a range of deletion mutants such as SOCS box molecules carrying deletion in the carboxy terminal region, the amino terminal region and in both the carboxy and amino terminal regions. Molecules are also contemplated by the present invention which encompasses only the carboxy terminal region or amino terminal region or fused to another peptide, polypeptide or protein.

As stated above, the present invention contemplates agonists and antagonists of the SOCS box. One example of an antagonist is an antisense oligonucleotide sequence. Useful oligonucleotides are those which have a nucleotide sequence complementary to at least a portion of the protein-coding or "sense" sequence of the nucleotide sequence. These antisense nucleotides can be used to effect the specific inhibition of gene expression. The antisense approach can cause inhibition of gene expression apparently by forming an antiparallel duplex by complementary base pairing between the antisense construct and the targeted mRNA, presumably resulting in hybridisation arrest of translation. Ribozymes and co-suppression molecules may also be used. Antisense and other nucleic acid molecules may first need to be chemically modified to permit penetration of cell membranes and/or to increase their serum half life or otherwise make them more stable for in vivo administration. Antibodies may also act as either antagonists or agonists although are more useful in diagnostic applications or in the purification of SOCS box peptides. Antagonists and agonists may also be identified following natural product screening or screening of libraries of chemical compounds or may be derivatives or analogues of the SOCS molecules.

Accordingly, the present invention extends to analogues of the SOC box peptides of the present invention. Analogues may be used, for example, in the treatment or prophylaxis of cytokine mediated dysfunction such as autoimmunity, immune suppression or hyperactive immunity or other condition including but not limited to dysfunctions in the haemopoietic, endocrine, hepatic and neural systems. Dysfunctions mediated by other signal transducing elements such as hormones or endogenous or exogenous molecules, antigens, microbes and microbial products, viruses or components thereof, ions, hormones and parasites are also contemplated by the present invention. They may also be useful in promoting degradation or inhibiting degradation.

Analogues of the proteins contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecule or their analogues.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitization, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other band, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid, contemplated herein is shown in Table 1.

TABLE 1

| Non-conventional amino code | Code |
| --- | --- |
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmrpo |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |

TABLE 1-continued

| Non-conventional amino code | Code |
|---|---|
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl) carbamylmethyl)glycine | Nnbhm |
| 1-carboxy-1-(2,2-diphenyl-ethylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcyclopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |

TABLE 1-continued

| Non-conventional amino code | Code |
|---|---|
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cylcododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl) carbamylmethyl)glycine | Nnbhe |

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

These types of modifications may be important to stabilise molecules comprising a SOCS box if administered to an individual or if used as a diagnostic reagent.

Other derivatives contemplated by the present invention include a range of glycosylation variants from a completely unglycosylated molecule to a modified glycosylated molecule. Altered glycosylation patterns may result from expression of recombinant molecules in different host cells.

Expression includes transcription or translation or both.

Another aspect of the present invention contemplates a method of modulating activity of SOCS in a human, said method comprising administering to said mammal an effective amount of a molecule for a time and under conditions sufficient to increase or decrease elongin B and/or elongin C binding to a SOCS box. The molecule may be a proteinaceous molecule or a chemical entity and may also be a derivative of SOCS or a chemical analogue or truncation mutant of SOCS.

Still a further aspect of the present invention contemplates a method of modulating levels of a SOCS protein in a cell said method comprising contacting a cell containing a SOCS gene with an effective amount of an inhibitor of elongin B- and/or elongin C-interaction with a SOCS box encoded by said SOCS gene for a time and under conditions sufficient to modulate levels of said SOCS protein.

Yet a further aspect of the present invention contemplates a method of modulating signal transduction in a cell containing a SOCS gene comprising contacting said cell with an effective amount of an inhibitor of elongin B and/or elongin C interaction with a SOCS box encoded by said SOCS gene for a time sufficient to modulate levels of SOCS protein with the cell.

Still a further aspect of the present invention contemplates a method of modulating the activity of a cytokine or cytokine-like molecule, said method comprising administering to a subject a modulating effective amount of a molecule for a time and under conditions sufficient to increase or decrease the biological activity of a complex comprising two or more of a SOCS box-containing peptide, polypeptide or protein; elongin B and/or C, elongin A and/or VHL. The molecule may be a proteinaceous molecule or a chemical entity and may also be a derivative of a polypeptide of the complex or its ligand.

The present invention, therefore, contemplates a pharmaceutical composition comprising the complex or a modulator of complex activity and one or more pharmaceutically acceptable carriers and/or diluents. These components are referred to as the "active ingredients".

The pharmaceutical forms suitable for injectable use include sterile aqueous solutions (where water soluble) and sterile powders for the extemporaneous preparation of sterile injectable solutions. It must be stable under the condition is of manufacture and storage and must be preserved against the contaminating action of microorganisms such as bacteria and fungi. The carrier can be a solvent or dilution medium comprising, for example, water, ethanol, polyol (for example, glycerol, propylene glycol and liquid polyethylene glycol, and the like), suitable mixtures thereof, and vegetable oils. The proper fluidity can be maintained, for example, by the use of superfactants. The preventions of the action of microoganisms can be brought about by various antibacterial and antifungal agents, for example, parabens, chlorobutanol, phenol, sorbic acid, thirmersol and the like. In many cases, it will be preferable to include isotinic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, baccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 μg and 2000 mg of active compound. Alternative dosage amounts include from about 1 μg to about 1000 mg and from about 10 μg to about 500 mg.

The present invention also extends to forms suitable for topical application such as creams, lotions and gels as well as a range of "paints" which are applied to skin and through which the active ingredients are absorbed. In addition, the complex or components thereof may be associated with penetration or the TAT protein of HIV.

Pharmaceutically acceptable barriers and/or diluents include any and all solvents, dispersion media, coatings, antibacterial and antifungal agents, isotonic and absorption delaying agents and the like. The use of such media and agents for pharmaceutical active substances is well known in the art and except insofar as any conventional media or agent is incompatible with the active ingredient, their use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable barrier in dosage unit form as hereinbefore disclosed. A unit dosage form can, for example, contain the principal active compound in amounts range from 0.5 μg to about 2000 mg. Expressed in proportions, the active compound is generally present in from about 0.5 µg to about 2000 mg/ml of carrier. In the case of compositions containing supplementary active ingredients, the dosages are determined by reference to the usual dose and manner of administration of the said ingredients.

Dosages may also be expressed per body weight of the recipient. For example, from about 10 ng to about 1000 mg/kg body weight, from about 100 ng to about 500 mg/kg body weight and for about 1 µg to above 250 mg/kg body weight may be administered.

The pharmaceutical composition may also comprise genetic molecules such as a vector capable of transfecting target cells where the vector carries a nucleic acid molecule capable of modulating levels of polypeptides involved in the complex. The vector, may, for example, be a viral vector.

The present invention provides, therefore, a mechanism for promoting termination of cytokine-signalling or for facilitating cytokine-signalling. Accordingly, another aspect of the present invention is directed, therefore, to the use of one or more of:—

(i) elongin B or a functional equivalent or chemical analogue thereof;
(ii) elongin C or a functional equivalent or chemical analogue thereof;
(iii) elongin A or a functional equivalent or chemical analogue thereof;
(iv) VHL or a functional equivalent or chemical analogue thereof;
(v) a peptide, polypeptide or protein comprising a SOCS box;
(vi) an agonist or antagonist of one or more of (i)–(v);
(vii) an agonist or antagonist of a complex formed by two or more of (i) to (v);
(viii) a chemical analogue or derivative of one or more of (i)–(vii);

in the manufacture of a medicament in the treatment of a condition in a subject.

The subject is preferably a human but may also be a primate, livestock animal (e.g. cow, sheep, horse, pig, goat), laboratory test animal (e.g. mouse, rat, guinea pig, hamster), companion animal (e.g. cat, dog) or captive wild animal.

The present invention further provides an animal model useful for assessing potential agonists and antagonist of complex formation.

Accordingly, another aspect of the present invention provides a genetically modified animal comprising a mutation in genetic material encoding a SOCS-box-containing protein such that said SOCS-box in said SOCS-box containing protein is not capable of functionally interacting with one or more of elongin A, B or C, VHL or a cytokine or cytokine-like molecule.

Reference herein to "functionally interacting" includes reference to the complex formation between a SOCS box and elongin B, C or A, and/or VHL leading to termination of cytokine- or cytokine-like molecule mediated signalling.

Preferably, the genetically modified animal is laboratory test animal such as a mouse, rat or hamster.

Preferably, the genetic modification comprises a single or multiple nucleotide substitution, addition and/or deletion to a region encoding the SOCS box or a region affecting SOCS box conformation.

Reference herein to a "cytokine-like molecule" includes reference to a molecule which comprises cytokines similar to or commonly associated with a cytokine. A "cytokine-like molecule" may also be a cytokine.

The present invention is further described by the following non-limiting Figures and Examples.

In the figures:—

FIGS. 1A–1B are photographic representations showing purification of SOCS box-binding proteins from murine myeloid M1 cells. FIG. 1A, SDS-PAGE (14% w/v Novex gel) analysis of affinity column eluates from GST-Sepharose column (lane 1), from GST-SOCS-1-SOCS-box-Sepharose column (lane 2), and from GST-SOCS-3-SOCS-box-Sepharose column (lane 3). The proteins were visualized by Coomassie blue staining. Arrows in lane 2 indicate the positions of the two protein bands excised for sequencing analysis by mass spectrometry. The molecular mass markers (in kilodaltons) are shown on the left. FIG. 1B, Western blot analysis of the three affinity column eluates mentioned in panel A by anti-rat elongins B and C antibodies. Anti-rat elongins B and C antibodies (cross react with murine and human elongins B and C) were purchased from Santa Cruz and used as a mixture of antibodies.

Figure 2:
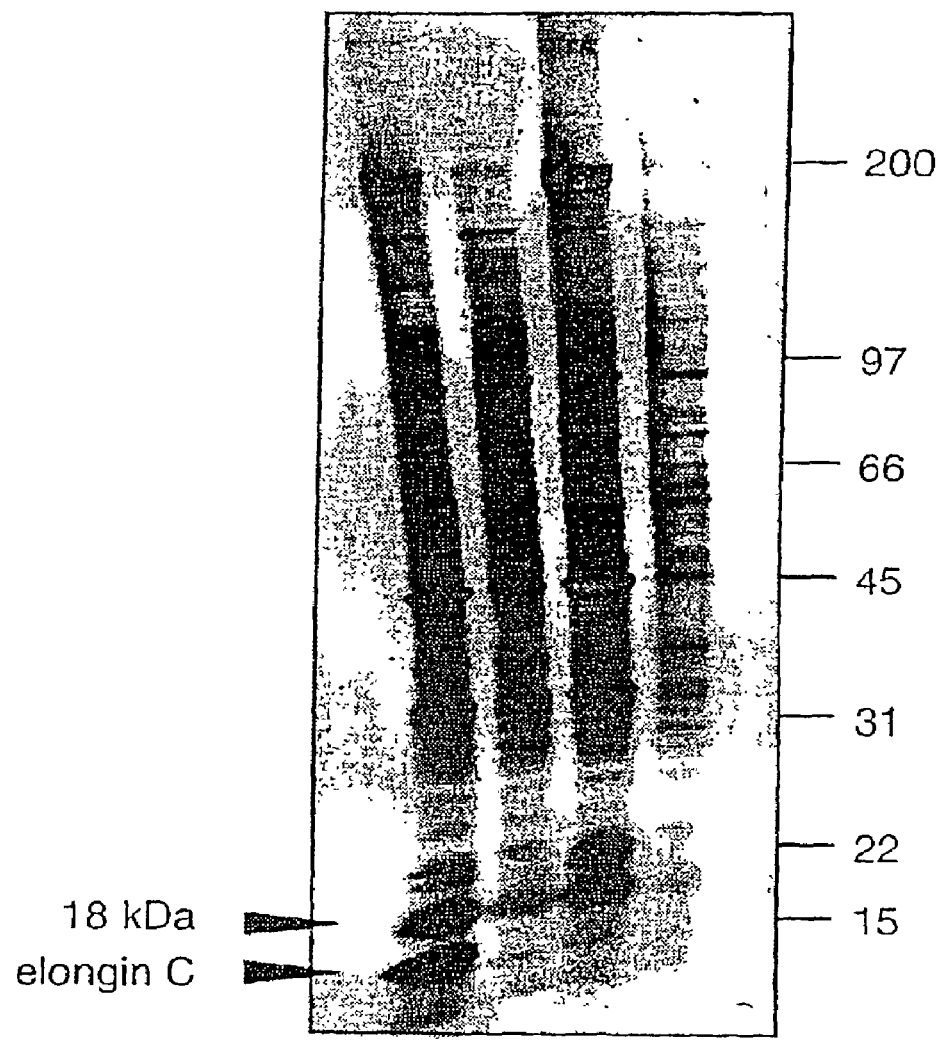
Figure 3:
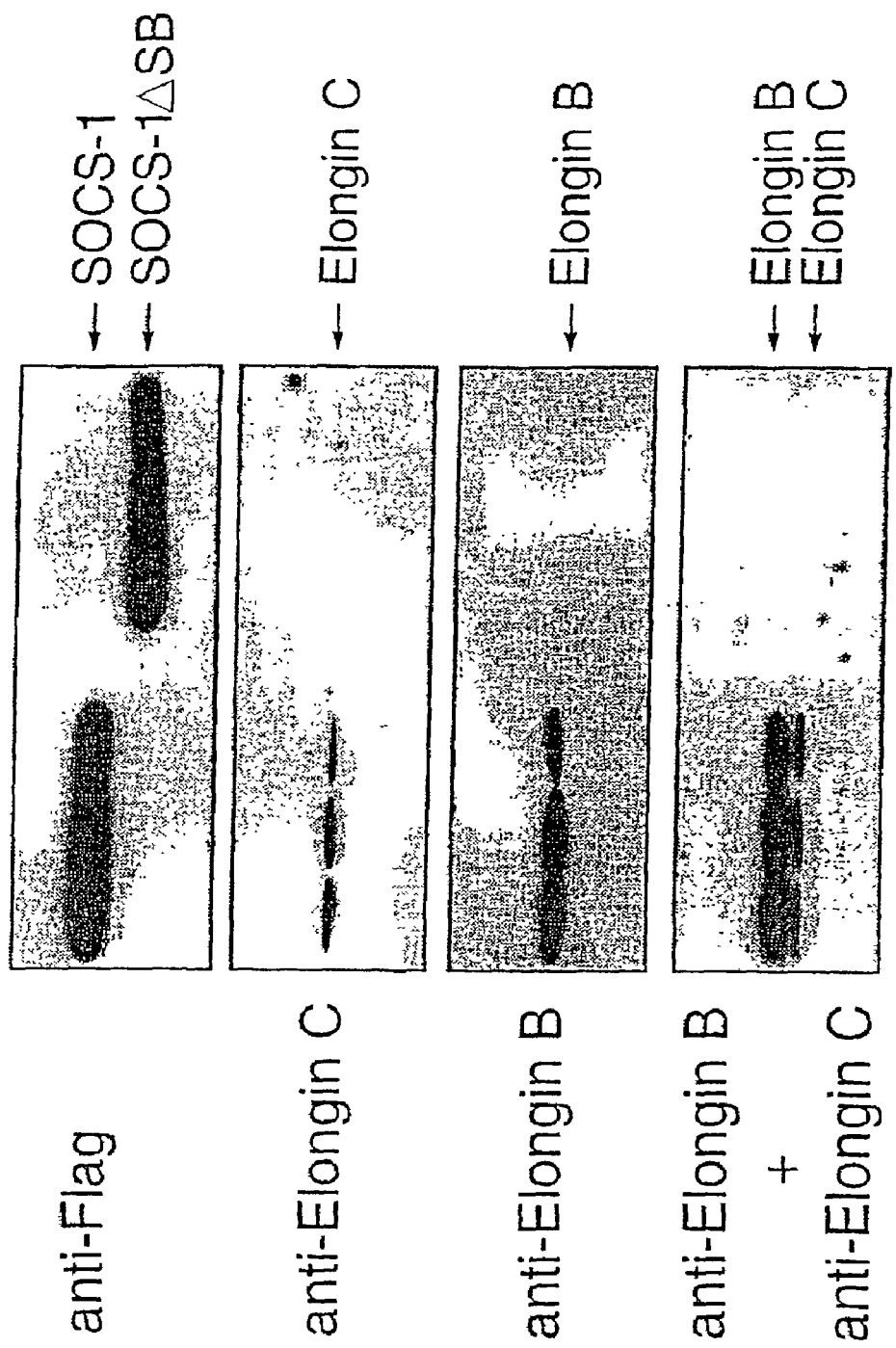

FIG. 2 is a photographic representation showing competition of SOCS-1 SOCS box interaction with elongin C. Biotinylated SOCS-1 SOCS box peptide was immobilized on streptavidin-agarose resin and used to affinity purify interacting proteins from M1 cellular extracts in the presence (+) or absence (–) of 80 mM competing non-biotinylated SOCS box peptides. Proteins were separated by SDS-PAGE on a 4–15% w/v acrylamide gel, and bands were visualized by silver staining. Soluble SOCS box peptides corresponding to SOCS-1, ASB-2 and WSB-2 prevented binding of elongin C to immobilized SOCS-1 SOCS box FIG. 3 is a photographic representation showing interaction of SOCS-1 with endogenous elongins B and C. Cellular extracts from M1 cells stably expressing either full-length SOCS-1 or SOCS-1 lacking SOCS box (both proteins were N-terminally FLAG-tagged) were incubated with anti-FLAG antibody M2 resin and bound cellular proteins were eluted from the columns with FLAG peptide as described in Materials and Methods. Lanes 1–3 correspond to column eluates 3 to 5 from M1 cells expressing full-length SOCS-1 and lanes 4–6 correspond to column eluates 3 to 5 from M1 cells expressing SOCS-1 lacking SOCS box. The panels from top to bottom correspond to Western blot analyses by anti-FLAG, anti-elongin C, anti-elongin B, and a mixture of anti-elongin B and anti-elongin C, respectively.

Figure 4:
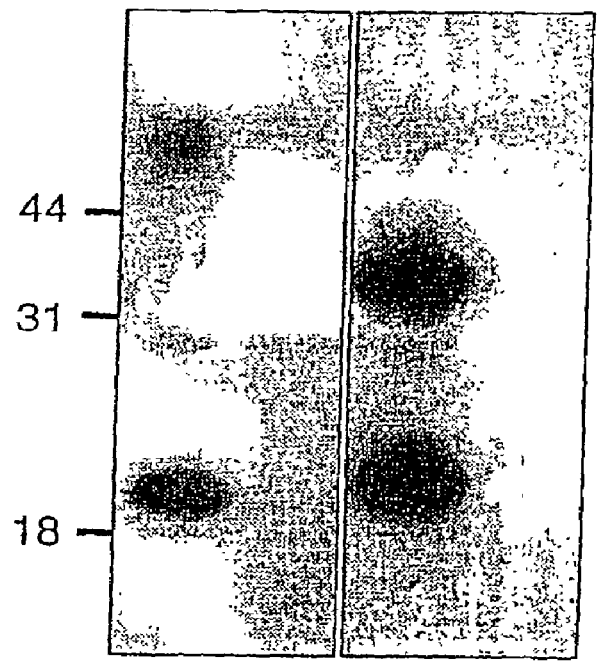
Figure 4:
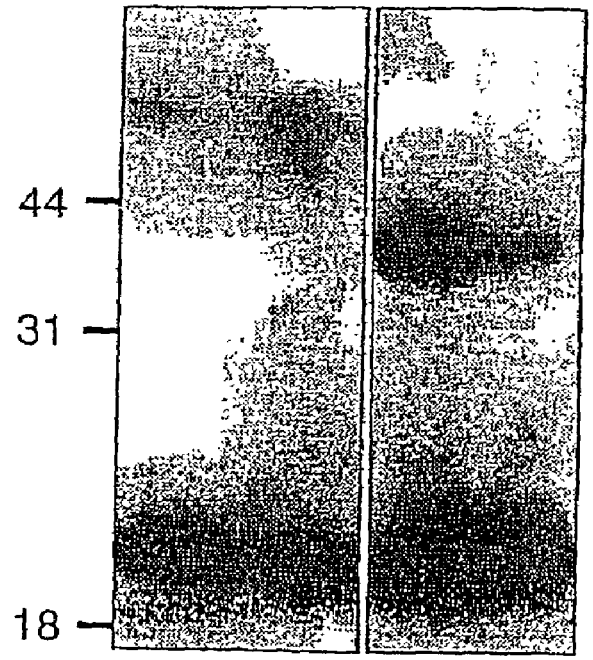

FIG. 4 is a representation showing co-transfection of 293T cells with SOCS and elongins B and C.

Figure 5:
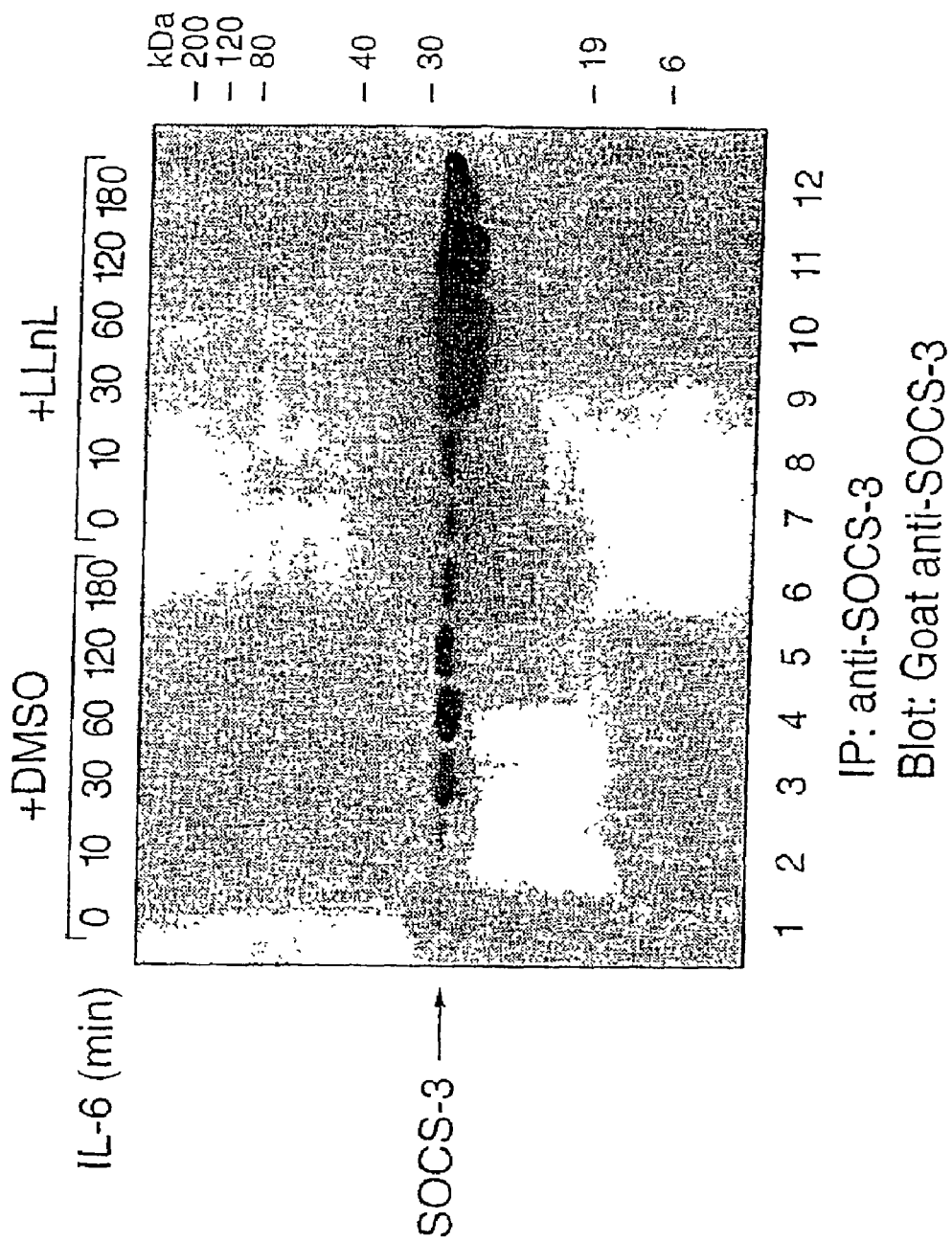

FIG. 5 is a photographic representation of the effect of LLnL on the endogenous expression of SOCS-3 protein. The murine macrophage-like J774 cells ($4\times10^7$) were treated with either DMSO (0.1% w/v) or LLnL (50 µM) for 15 min and then stimulated with 100 ng/ml of murine IL-6 for the indicated times in the presence of DMSO or LLnL during stimulation. The cellular extracts were immunoprecipitated with a rabbit-anti-SOCS-3 polyclonal antiserum and immune complexes eluted from protein G-Sepharose beads were resolved by SDS-PAGE (13% w/v) under reducing conditions and analysed by Western blot using biotinylated rabbit-anti-SOCS-3.

FIG. 6 is a diagrammatic representation providing a model of the interaction of SOCS box-containing proteins with elongins C and B (upper panel) and comparison with the phosphoprotein ubiquitin ligase complex (PULC) assembled by F box-containing proteins (lower panel).

Figure 7A:
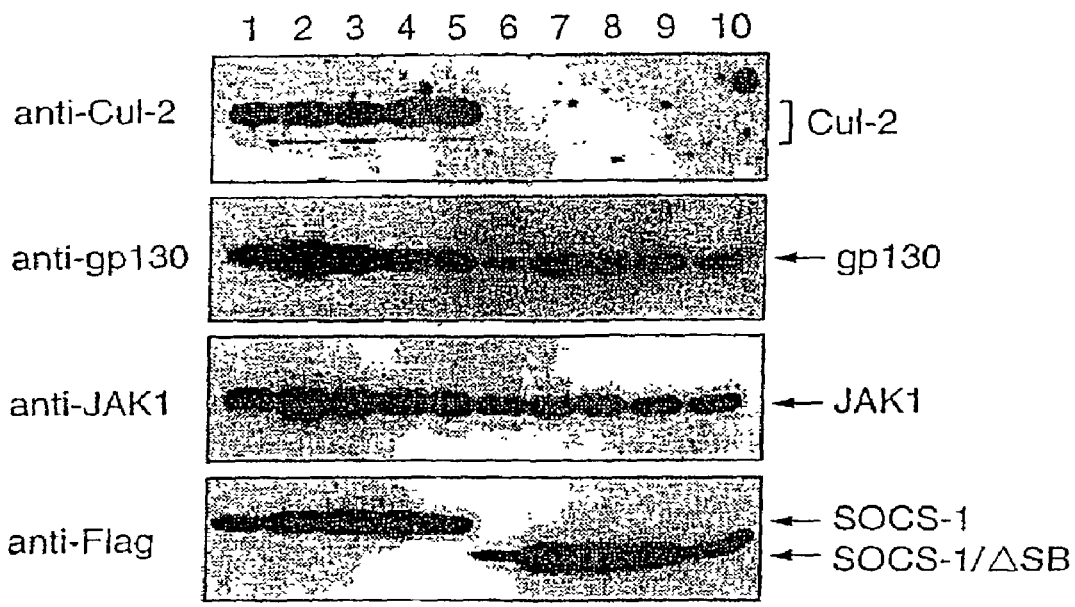
Figure 7B:
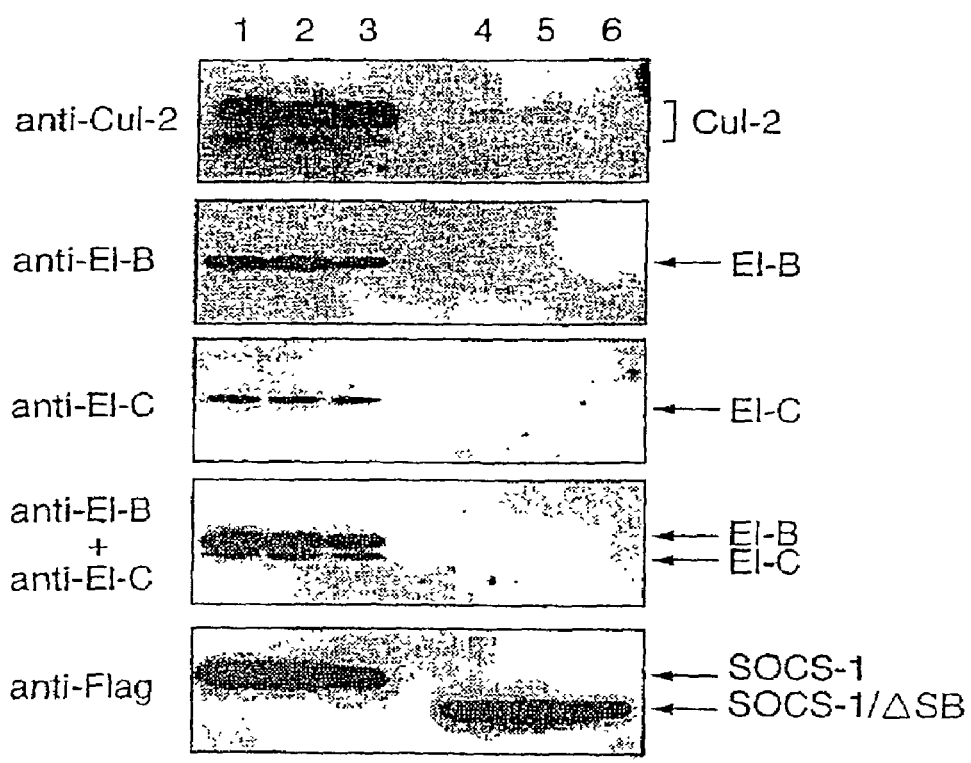

FIGS. 7A–7B are photographic representations showing M1 cells expressing FLAG-tagged SOCS-1 (lanes 1–5 (FIG. 7A) and 1–3 (FIG. 7B)) or FLAG-tagged SOCS-1 lacing a SOCS box (lanes 6–10 (FIG. 7A) and 4–6 (FIG. 7B)) were lysed. Lysates were then purified on an anti-flag affinity column and eluted and subjected to SDS-PAGE. Gels were blotted and membranes were then probed with antisera to the indicated proteins.

Figure 8:
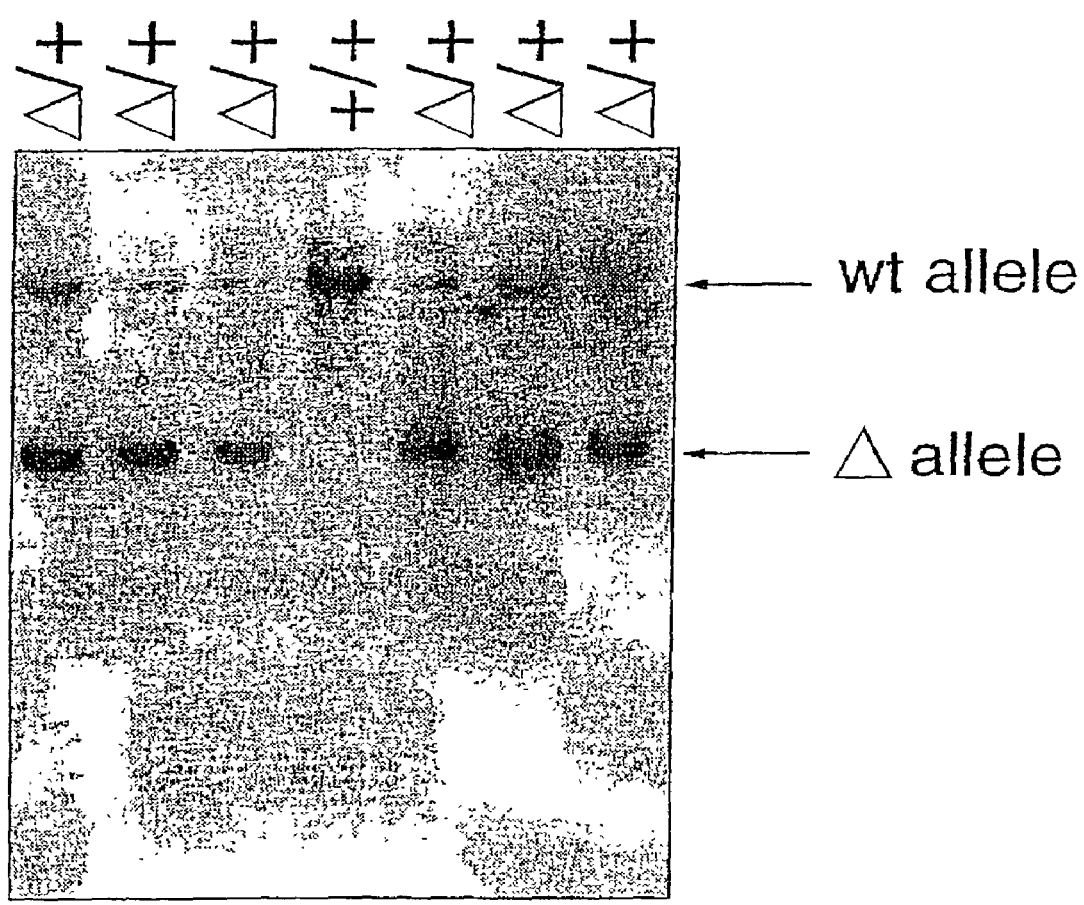

FIG. 8 is a photograhic representation showing chimeric mice which were derived from injection of ES cells containing the correct deletions of the SOCS box in SOCS-1 into blastocytes. Chimeras were moited with C57BL/6 and DNA from the progeny was prepared, digested with EcoRV and probed with a 700 bp NheI/BamHI fragment from the 5' end of the SOCS-1 gene. The wild type of approximately 20 kb and the targeted allele (Δ) of 3.5 kb are indicated.

EXAMPLE 1

SOCS and Elongin Expression Vectors

The cDNAs encoding mouse SOCS-1, SOCS-3, WSB-1, SSB-1, ASB-1, have been described previously (1,8). Constructs in pEF-FLAG1 encoding these proteins, with or without the SOCS box, with an N-terminal FLAG epitope tag (DYKDDDDK) (SEQ ID NO:1) were generated by PCR essentially as described (8) (found at http://www-.wehi.edu.au/willson vectors). DNA fragments encoding mouse elongins B and C were amplified using PCR from a 17-day embryo cDNA lambda library (Clontech ML5014t) and were expressed with N-terminal FLAG or myc (DQK-LISEEDL) (SEQ ID NO:2) epitope tags, respectively, using the mammalian expression vector pEF-BOS.

EXAMPLE 2

Stable and Transient Transfection of Cell Lines

The murine monocytic leukemic cell line, M1, and the 293T human fibroblast cell line were maintained and transfected as described (8).

EXAMPLE 3

Preparation or GST and GST-SOCS Box Affinity Resins

DNA fragments encoding the SOCS boxes from mouse SOCS-1 (residues 172–212) and SOCS-3 (residues 186–225) with an N-terminal linker sequence (EGKSSGSG-SESKVD) (SEQ ID NO:3) were generated by PCR and cloned into the bacterial expression vector pGEX-2T (9). The GST fusion proteins were purified by affinity chromatography on glutathione Sepharose 4B (Amersham Pharmacia Biotec) and affinity resins were prepared by covalently coupling 1 mg of purified proteins to 1 ml of NHS-activated Sepharose resin (Amersham Pharmacia Biotec). Before use, the affinity resins were washed with elution buffer (0.5% w/v SDS, 50 mM DTT, 50 mM Tris-HCl, pH 8.0 and 150 mM NaCl) and equilibrated in lysis buffer (0.5% w/v Nonidet P-40, 10 mM Tris-HCl, pH 7.5 and 100 mM NaCl).

EXAMPLE 4

Purification of SOCS Box-Binding Proteins

M1 cells ($2 \times 10^{10}$) were lysed on ice for 30 min in 100 ml of lysis buffer supplemented with protease inhibitors (Complete Cocktail tablets; Boehringer Mannheim, Mannheim, Germany), 1 mM PMSF, 1 mM $Na_3VO_4$ and 1 mM NaF. The total cell lysate was centrifuged at 15,000 rpm (SS34 rotor) for 15 min at 4° C. and the clarified supernatant pre-incubated with 1 ml of GST-Sepharose resin for 2 h at 4° C. Half the GST-Sepharose-depleted M1 cell lysate was incubated with 1 ml of GST-SOCS-1 SOCS box- and the other half with GST-SOCS-3 SOCS box-Sepharose resin for 2 h at 4° C. The affinity resins were washed with 40 ml of lysis buffer and then eluted with 8×0.5 ml of elation buffer. Eluates were concentrated to ~40 μl, mixed with 15 μl of 4×SDS sample buffer containing 0.4 M DTT and resolved on a 14% polyacrylamide gel (Novex). The gel was stained for 5 min with 0.1% w/v Coomassie blue in 50% w/v methanol and destained in 12% w/v methanol and 7% w/v acetic acid.

EXAMPLE 5

Protein Identification by Peptide Mass Fingerprinting

Protein bands were excised from the Coomassie blue-stained gel and in-situ tryptic digestion was performed as described previously (10). An electrospray ion trap mass spectrometer (LCQ Finnigan MAT, San Jose, Calif.) coupled on-line to a capillary HPLC (11,12) was used for peptide sequencing. The sequences of individual peptides were identified manually or by using the SEQUEST algorithm (incorporated into the Finnigan-MAT BIOWORKS™ software) to correlate the collision-induced dissociation spectra with amino acid sequences in the OWL protein database (13).

EXAMPLE 6

Peptide Synthesis and Biotinylation

Peptide fragments of murine SOCS-1, WSB-2 and ASB-2 corresponding to the SOCS boxes and five upstream N-terminal residues (1 were synthesized according to the in situ neutralization/HBTU activation protocol for Boc solid phase chemistry (14, purified using reverse phase HPLC and the products characterized by electrospray mass spectrometry. A sample of the SOCS-1 SOCS box peptide was post-synthetically biotinylated by treatment with sulfosuccinimidobiotin. Prior to biotinylation, the sidechain of the unique cysteine residue was temporarily protected by oxidation to the peptide disulfide dimer. The SOCS-1 SOCS box peptide contains no lysine residues, thus excess biotinylation reagent was used to completely and specifically modify the amino terminus. Following biotinylation, the peptide was reduced by treatment with 5 mM DTT. Typically, peptide was coupled to streptavidin-agarose resin (Pierce immunopure; 1–2 mg streptavidin/mL resin) by incubating equal volumes of resin and 1 mg/mL peptide for 1 h, followed by extensive washing.

EXAMPLE 7

Competition of SOCS 1 SOCS Box/Elongin C Interaction

M1 cells were lysed as previously described, except at a concentration of $10^9$ cells/mL of lysis buffer. Streptavidin-agarose binding proteins were precleared from lysate by treating overnight at 4° C. with streptavidin-agarose resin (100 μL of resin/mL lysate). SOCS box peptides (SOCS-1, ASB-2 and WSB-2) were solubilized in water at 10 mg/mL, and aliquots of these, or water alone, were added to 350 μL fractions of cleared lysate, followed by incubation for 3 h at 4° C. These lysates were then added to 30 μL of SOCS-1 SOCS box peptide resin and incubated a further 2 h at 4° C. The resin was extensively washed with lysis buffer and bound proteins were eluted with 20 μL of 4×SDS sample buffer. Proteins were separated by SDS-PAGE on a 4–15% reducing gel.

EXAMPLE 8

Detection of SOCS-1 Interaction with Endogenous Elongins

Two liters of M1 cells stably expressing either full-length SOCS-1 or SOCS-1 lacking SOCS box (with N-terminal FLAG epitopes) were grown in DME containing 5% bovine calf serum, 10 μg/ml puromycin and 50 ng/ml murine IL-6. The cells were harvested and incubated in 20 ml of culture media containing 10 μM proteasome-specific inhibitor, N-acetyl-L-leucinyl-L-leucinyl-norleucinal (LLnL; Sigma, St. Louis, Mo.) for 30 min at 37° C. The cells were lysed in 14 ml of lysis buffer supplemented with protease inhibitors (Complete Cocktail tablets), 1 mM PMSF, 1 mM $Na_3VO_4$, 1 mM NaF and 10 μM LLnL. Total cell lysates were centrifuged at 15,000 rpm (SS34 rotor) for 15 min at 4° C. and the clarified supernatants incubated with 0.3 ml of M2 anti-FLAG antibody resin for 3 h at 4° C. Resin was then washed with 10 ml of lysis buffer and the bound proteins were eluted with 6×150 μl of 100 μg/m FLAG peptide in lysis buffer.

EXAMPLE 9

IL-6-Induced Expression of Endogenous SOCS-3 Protein

Mouse macrophage-like J774 cells were grown continuously in DME containing 10% bovine calf serum. The cells were washed once in PBS, twice with DME and starved for 1 h in DME containing 0.1% w/v low-endotoxin bovine serum albumin (BSA; Sigma). The proteasome inhibitor LLnL dissolved in dimethyl sulfoxide (DMSO) or DMSO was added to the cells for 15 min and the cells then stimulated with 100 ng/ml of murine IL-6 for the indicated times.

EXAMPLE 10

Co-Immunoprecipitation and Western Analysis

Proteins were immunoprecipitated with anti-myc (9E10; WEHI) and protein A-Sepharose or anti-FLAG antibody conjugated to Sepharose (KM5-IC7; WEHI) and separated by sodium dodecyl sulphate-polyacrylamide gel electrophoresis (SDS-PAGE) (Biorad, Hercules, Calif.) under reducing conditions. Proteins were then electrophoretically transferred to PVDF-Plus membranes (Micron Separations Inc. WestBorough, Mass.) and Western blotted as described (8).

EXAMPLE 11

Analysis of SOCS Box

Although the SOCS box appears to be a modular sequence motif present in at least twenty different proteins it does not appear to be required for inhibition of the JAK/STAT signalling pathway when SOCS proteins are overexpressed (7,8). The inventors reasoned that the SOCS box might play a regulatory role in targeting proteins to particular cell compartments or in controlling the in vivo half-lives of proteins which may become important considerations when SOCS proteins are expressed at physiological levels. The SOCS box domain is unlikely to be large enough to encode catalytic activity and is therefore likely to mediate such effects through protein—protein interactions. Consequently, the ability of the SOCS box to interact with cellular target proteins was investigated.

Isolated SOCS box sequences were used as affinity reagents to identify interacting proteins in cell lysates. Glutathione-5-transferase (GST) fusion proteins containing the SOCS box sequences from SOCS-1 or SOCS-3 were coupled to Sepharose beads and used as affinity resins to bind proteins from M1 cell lysates. After washing the beads, bound proteins were eluted with SDS buffer and electrophoresed on SDS-PAGE gels followed by staining with Coomassie Blue. The most prominent bands seen binding to both GST-SOCS fusion proteins but not the GST control were proteins of 15 and 18 kDa (FIG. 1). These bands were excised from the gel and digested in situ with trypsin. Tryptic peptides were separated by reverse-phase capillary HPLC and the column eluate fed directly onto a electrospray ion trap mass spectrometer. Collision-induced dissociation of the molecular ions was used to determine the amino acid sequences of the tryptic fragments and these were correlated against sequences in the OWL protein data base. The 18 kDa band generated 10 peptides that could be identified as belonging to elongin B and the 15 kDa band generated 5 peptides that could be identified as belonging to elongin C (Table 1). Western blotting of the gels of the same eluates with antibodies against elongins B and C confirmed that both elongins were present in eluates from beads containing SOCS-1 or SOCS-3-box fusion proteins but not from control GST bands (FIG. 1).

Similar experiments using a biotinylated SOCS-1 SOCS box peptide bound to streptavidin-agarose also resulted in the identification by mass spectrometry of elongins B and C as interacting proteins in M1 cellular extracts. The specificity of this interaction was tested by pre-incubating extracts with unbiotinylated SOCS box peptides prior to addition of the imobilized SOCS-1 SOCS box peptide. As expected, unconjugated SOCS-1 SOCS box peptide competed for this interaction as did SOCS box peptides from, WSB-2 and ASB-2 suggesting that interaction with elongins B and C is a general property of the conserved SOCS box (FIG. 2). Interestingly, identical results were obtained whether M1 cells were stimulated with cytokine (IL-6 or LIF) or not.

The inventors next tested the capacity of full-length or SOCS box-deleted SOCS proteins to interact with elongins B and C in M1 cells. M1 cells stably transfected with vectors encoding N-terminally FLAG-tagged full-length SOCS-1 or SOCS-1 lacking a SOCS box (SOCS-1/ΔSB) were lysed, the FLAG-tagged proteins were immunoprecipitated with anti-FLAG M2 antibody beads and the beads were eluted with FLAG peptide. The eluates were electrophoresed on SDS-PAGE gels, transferred to PVDF membranes and Western blotted with anti-FLAG antibodies or antibodies to elongins B and C (FIG. 3). Although full-length SOCS-1 and SOCS-1/ΔSB were expressed at similar levels, only the full-length SOCS-1 protein was associated with bound elongins B and C.

To further confirm the generality of this interaction for other proteins containing a SOCS box, 293T fibroblasts were transfected with N-terminally FLAG-tagged WSB-2 or SSB-1 along with elongin B containing a FLAG epitope or elongin C containing a myc epitope. When elongin C was immunoprecipitated with anti-myc antibodies and the electrophoresed eluates Western blotted with anti-FLAG antibodies, both WSB-2 and SSB-1 were found to co-immunoprecipitate along with elongin B with elongin C (FIG. 4). As with SOCS-1, the interaction of elongins B and C with SSB-1 was dependent on the SOCS box as a truncated form lacking only the SOCS box failed to co-immunoprecipitate with the elongins (FIG. 4).

Because elongins B and C have been proposed to target proteins to proteasomal destruction (15,16), the inventors tested whether endogenous SOCS proteins are degraded through the proteasomal complex. When the J774 macrophage cell line was stimulated with IL-6, SOCS-3 protein expression was elevated by 30 min, peaked at 60 min and was significantly depleted by 120 and 180 min. In contrast, cells incubated with the proteasomal inhibitor LLnL and stimulated with IL-6 showed a continual increase in SOCS-3 protein levels from 30–180 min (FIG. 5) suggesting that the proteasomal complex plays a major role in rapidly degrading SOCS-3 after its induction.

EXAMPLE 12

Analysis of Proteins Interacting with the SOCS Box

The inventors passed lysates from $10^9$ unstimulated M1 cells expressing FLAG-tagged SOCS-1 through an anti-FLAG affinity column which was then eluted with FLAG peptide. The eluate was then subjected to SDS-PAGE and the proteins were Western blotted. The blot was then probed with anti-FLAG antibodies to confirm the presence of SOCS-1 and with a range of antibodies against proteins thought to interact with SOCS-1 (FIG. 7). It can be seen that SOCS-1 is capable of forming a complex with elongin B and elongin C, cullin 2, as well as JAK1 and gp130. To determine whether proteins in this complex interact directly or indirectly with SOCS-1, or whether all the proteins can be found together in a single complex, or whether separate complexes are, for example, formed between SOCS-1, JAK-1 and gp130 on one hand and between SOCS-1, elongin B and C and cullin-2, is addressed in part by performing the primary immunoprecipitation using a different antibody. For example, if immunoprecipitation with an anti-gp130 antibody only results in co-precipitation of JAK1 and SOCS-1, then this would suggest that SOCS-1 may form different complexes.

Further, the nature of the complex is analyzed by repeating experiments using a mutant SOCS protein which lacks one or more domains. In the case described above, the inventors have performed an identical analysis using M1 cells expressing a FLAG-tagged mutant of SOCS-1 lacking the SOCS box. In this case, while JAK1 and gp130 are still shown to associate with the mutant, no evidence of interaction with elongin B, elongin C or cullin-2 is apparent. This type of experiment addresses whether interactions are direct or indirect. Further analysis involves approaches of the type described below.

EXAMPLE 13

Generation of Mice in which the SOCS Box has Been Deleted from the SOCS-1 Gene

One of the most important steps in assessing the importance of particular interactions is to translate biochemical and biophysical studies back into a physiological setting. The generic approach the inventors are taking to achieve this is to generate "knock-ins" to specifically disrupt the interaction of SOCS proteins with particular partners. The type of mutation engineered into the mouse germline is very much dependent on the specific question being addressed. To provide a tangible example of this approach, a mouse in which the SOCS-box of SOCS 1 has been deleted is generated to allow the role of the SOCS box interaction with the elongin B and C complex to be addressed in a physiological induction system in vivo.

To construct a targeting vector for the precise deletion of the SOCS-1 SOCS box, overlap PCR used to generate a 2.7 kb BamHI genomic fragment spanning the coding exon, in which the sequence encoding the SOCS box is deleted. This fragment is used as a 5' arm in a vector containing PGKneo cassette and a 3.2 kb BamHI/EcoRV 3' arm fragment. C57B1/6 ES cell clones in which this targeting vector is recombined with the endogenous SOCS-1 gene are identified via Southern blot analysis of EcoRV-digested genomic DNA with the probe used to diagnose targeting in the conventional SOCS-1 knockout. This allows distinction between the endogenous (20 kb) and SOCS-1-SOCS box-deleted (SOCS-1 $\Delta$, 3.5 kb) loci. Two targeted ES cell clones are injected into Balb/c blastocysts to generate germline chimeric mice, from which SOCS-1 $\Delta/\Delta$ mice are bred to yield heterozygous ($\Delta/+$) mice (FIG. 8). This colony is expanded and is used to, for example, to generate homozygote ($\Delta/\Delta$) mice.

Heterozygous mice provide an ideal tool for examining the role of the SOCS box in influencing protein stability. Two hypotheses are put forward, one suggesting that the SOCS box targets proteins for degradation, the other that it protects proteins from degradation. These hypotheses are tested by growing primary bone marrow macrophages and embryonic fibroblasts from SOCS-$1^{\Delta/+}$ mice and SOCS-$1^{\Delta/+}$, stimulating the cells with cytokines such as IL-6 or IFN$\gamma$ and using a pulse-chase protocol, in which cells are metabolically labelled using $^{35}$S-methionine and chased using unlabelled methionine. This allows the half-lives of immunoprecipitated SOCS-1 and SOCS-1 lacking a SOCS box to be compared. This type of experiment is performed in a number of cells using a number of cytokines to induce expression of SOCS-1. It is also possible to perform this type of study on thymocytes taken directly from mice, since these cells appear to constitutively express SOCS-1.

In addition to providing cells for experimental work, SOCS-$1^{\Delta/+}$ mice are interbred to generate SOCS-$1^{\Delta/\Delta}$ mice. Cohorts of SOCS-$1^{/+}$ and $\Delta/\Delta$ mice are set aside for full biological analyses of the type described for SOCS-$1^{-/-}$ animals. This is useful because if the SOCS box targets SOCS-1 for degradation then it will be important to know whether this is a mechanism by which signal transduction is negatively regulated (i.e. the JAK kinase bound to SOCS-1 is also degraded) or whether it is a mechanism by which negative regulation is relieved (i.e. free SOCS-1 is degraded). If the former is correct one might expect that SOCS-$1^{\Delta/\Delta}$ mice may have a less severe form of the phenotype observed for SOCS-$1^{-/-}$ mice (i.e. a partial loss-of-function phenotype). If the latter hypothesis is correct, then an opposite phenotype (i.e. partial gain-of-function) might be observed. As with simple SOCS-$1^{-/-}$ mice, if SOCS-$1^{\Delta/\Delta}$ mice die prematurely, they are crossed with IFN$\gamma^{-/-}$ mice to allow the effect of the SOCS box deletion to be examined in a number of cytokine systems using cells taken from healthy rather than sick animals.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

1. T. J., Alexander, W. S., Metcalf, D., Nicola, N. A. & Hilton, D. J. (1997) *Nature* (London) 387, 917–921.
2. Hilton, D. J., Richardson, R. T., Alexander, W. S., Viney, E. M., Willson, T. A., Sprigg, N. S., Starr, R., Nicholson, S. E., Metcalf, D.& Nicola, N. A. (1998) *Proc. Natl. Acad. Sci. USA* 95, 114–119.
3. Yoshimura, A., Ohkubo, T., Kiguchi, T., Jenkins, N. A., Gilbert, D. J., Copeland, N. G., Hara, T. & Miyajima, A. (1995) *EMBO J.* 14, 2816–2826.
4. Endo, T. A., Masuhara, M., Yokouchi, M., Suzuki, R., Mitsui, K., Sakamoto, H., Ohtsubo, M., Misawa, H., Kanekura, Y. & Yoshimura, A. (1997) *Nature* (London) 387,921–924.
5. Naka, T., Narazaki, M., Hirata, M., Matsumoto, T., Minamoto, S., Aono, A., Nishimoto, N., Kajita, T., Taga, T., Yoshizaki, K., Akira, S. & Kishimoto, T. (1997) *Nature* (London) 387, 924–929.
6. Masuhara, M., Sakamoto, H., Matsumoto, A., Suzuki, R., Yasukawa, H., Mitsui, K., Wakioka, T., Tanimura, S., Sasaki, A., Misawa, H., Yokouchi, M., Ohtsuba, M. & Yoshimura, A. (1997) *Biochem. Biophys. Res. Commun.* 239, 429–446.
7. Minamoto, S., Ikegame, K., Ueno, K., Narazaki, M., Naka, T., Yamamoto, H., Matsumoto, T., Saito, M., Hosoe, S. & Kishimoto, T. (1997) *Biochem. Biophys. Res. Commun.* 237, 79–83.
8. Narazaki, M., Fujimoto, M., Matsumoto, T., Morita, T., Saito, H., Kajita, T., Yoshizaki, K., Naka, T. & Kishimoto, T. (1998) *Proc. Natl. Acad. Sci. USA* 95, 13130–13134.
9. Smith, D. B. & Johnson, K. S. (1988) *Gene* 67, 31–40
10. Moritz, R. L., Eddes, J. S., Reid, G. E. & Simpson, R. J. (1996) *Electrophoresis* 17, 907–917.
11. Moritz, R. L., Reid, G. E., Ward, L. D. & Simpson, R. J. (1994) *Methods* 6, 213–226.
12. Zugaro, L. M., Reid, G. E., Ji, H., Eddes, J. S., Murphy. A. A., Burgess, A. W. & Simpson, R. J. (1998) *Electrophoresis* 19, 867–876.
13. Eng, J. K., McCormack, A. L. & Yates, J. R. (1994) *J. Am. Soc. Mass. Spectrom.* 5, 976–989.
14. Schnölzer, M., Alewood, P., Jones, A., Alewood, D. and Kent, S. B. H. *Int. J. Pept. Protein Res.,* 1992, 40, 180–193.
15. Kaelin Jr. W. G. & Maher, E. R. (1998) *Trends Gen.* 14, 423–426.
16. Conaway, J. W., Kamura, T. & Conaway, R. C. (1998) *Biochim. Biophys. Acta* 1377, M49–M54.
17. Garrett K. P., Aso, T., Bradsher, J. N., Foundling, S. I., Lane, W. S., Conaway, R. C. & Conaway, J. W. (1995) *Proc. Natl. Acad. Sci. USA* 92, 7172–7176.
18. Lonergan, K. M., Iliopoulos, O., Ohh, M., Kamura, T., Conaway, R. C., Conaway, J. W. & Kaelin, W. G. (1998) *Mol. Cell. Biol.* 18, 732–741.
19. Schauber, C., Chen, L., Tongaaokar, P., Vega, I., Lambertson, D., Potts, W. & Madura, K. (1998) *Nature* (London) 391, 715–718.
20. Duan, D. R., Pause, A., Burgess, W. H., Aso, T., Chen, D. Y. T., Garrett, K. P., Conaway, R. C., Conaway, J. W., Linehan, W. M. & Klausner, R. D. (1995) *Science* 269, 1402–1406.
21. Kibel, A., Iliopoulos, O., DeCaprio, J. D. & Kaelin, W. G. (1995) *Science* 269, 1444–1446.
22. Pause, A., Lee, S., Worrell, R. A., Chen, D. Y. T., Burgess, W. H., Linehan, W. M. & Klausner, R. D. (1997) *Proc. Natl. Acad. Sci. USA* 94, 2156–2161.
23. Kishida, T., Stackhouse, T. M., Chen, F., Lerman, M. I. & Zbar, B. (1995) *Cancer Res.* 55, 4544–4548.
24. Hershko, A. & Ciechanover, A. (1998) *Annu. Rev. Biochem.* 67, 425–479.
25. Verdier, F., Chretien, S., Muller, O., Varlet, P., Yoshimura, A., Gisselbrecht, S., Lacombe, C. & Mayeux, P. (1998) *J. Biol. Chem.* 273, 28185–28190.
26. Yu, C.-L. & Burakoff, S. J. (1997) *J. Biol. Chem.* 272, 14017–14020.
27. Terrell, J., Shih, S., Dunn, R. & Hicke, L. (1998) *Molecular Cell* 1, 193–202.

---

The invention claimed is:

1. A method of identifying a molecule which inhibits protein degradation in cells mediated by elongin C, comprising subjecting candidate molecules to an assay which detects the interaction between a SOCS box and elongin C wherein said SOCS box comprises the sequence, (T,S,P) LXXX(C,S)XXX(LIV) (SEQ ID NO:4), and selecting the molecule which inhibits said interaction wherein the selected molecule is a molecule which inhibits protein degradation in cells mediated by elongin C.

2. A method of identifying a molecule which promotes protein degradation in cells mediated by elongin C, comprising subjecting candidate molecules to an assay which detects the interaction between a SOCS box and elongin C wherein said SOCS box comprises the sequence, (T,S,P) LXXX(C,S)XXX(LIV) (SEQ ID NO:4), and selecting the molecule which promotes said interaction wherein the selected molecule is a molecule which promotes protein degradation in cells mediated by elongin C.

* * * * *